(12) United States Patent
Tang et al.

(10) Patent No.: US 12,383,763 B2
(45) Date of Patent: Aug. 12, 2025

(54) SYSTEMS AND METHODS FOR GENERATING TREATMENT PLANS

(71) Applicant: SHANGHAI UNITED IMAGING HEALTHCARE CO., LTD., Shanghai (CN)

(72) Inventors: Junxiang Tang, Shanghai (CN); Weiyuan Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 313 days.

(21) Appl. No.: 17/822,424

(22) Filed: Aug. 25, 2022

(65) Prior Publication Data

US 2023/0069291 A1    Mar. 2, 2023

(30) Foreign Application Priority Data

Aug. 25, 2021  (CN) .......................... 202110982536.8
Aug. 25, 2021  (CN) .......................... 202110984202.4
Nov. 24, 2021  (CN) .......................... 202111408059.0

(51) Int. Cl.
*A61N 5/10* (2006.01)
*G16H 20/40* (2018.01)

(52) U.S. Cl.
CPC ........... *A61N 5/1031* (2013.01); *G16H 20/40* (2018.01)

(58) Field of Classification Search
None
See application file for complete search history.

(56) References Cited

U.S. PATENT DOCUMENTS

| 7,801,270 | B2 | 9/2010 | Nord et al. |
| 8,085,899 | B2 | 12/2011 | Nord et al. |
| 10,307,615 | B2 | 6/2019 | Ollila et al. |
| 10,857,384 | B2 | 12/2020 | Ollila et al. |
| 2007/0263915 | A1 | 11/2007 | Mashiach |

(Continued)

FOREIGN PATENT DOCUMENTS

| CN | 102024097 A | 4/2011 |
| CN | 105404789 A | 3/2016 |

(Continued)

OTHER PUBLICATIONS

Yin, Xiangrui, Low-Dose Ct Image Processing And Reconstruction Using Deep Residual Network, A Thesis Submitted to Southeast University For the Professional Degree of Master of Engineering, 2019, 60 pages.

(Continued)

*Primary Examiner* — Marcus H Taningco
(74) *Attorney, Agent, or Firm* — METIS IP LLC

(57) ABSTRACT

The disclosure provides systems and methods for generating a treatment plan for irradiating a target region. The system may obtain at least one parameter from the treatment plan. The at least one parameter may relate to a dose region where is enclosed by an isodose curve. The system may obtain an objective function corresponding to the target region. The objective function may represent a conformity between the target region and the dose region. The system may further generate the treatment plan by optimizing the at least one parameter such that the objective function satisfies an optimization condition.

19 Claims, 11 Drawing Sheets

(56) References Cited

U.S. PATENT DOCUMENTS

| | | |
|---|---|---|
| 2009/0147909 A1 | 6/2009 | Yoda et al. |
| 2015/0238158 A1 | 8/2015 | Zhou et al. |
| 2017/0014642 A1 | 1/2017 | An et al. |
| 2018/0154177 A1 | 6/2018 | Bzdusek et al. |
| 2018/0264286 A1 | 9/2018 | Liu |
| 2021/0020297 A1* | 1/2021 | Adler ................ G06N 3/08 |
| 2022/0218298 A1 | 7/2022 | Gou et al. |
| 2023/0128148 A1 | 4/2023 | Li et al. |

FOREIGN PATENT DOCUMENTS

| | | |
|---|---|---|
| CN | 105893772 A | 8/2016 |
| CN | 106039599 A | 10/2016 |
| CN | 108364678 A | 8/2018 |
| CN | 109453473 A | 3/2019 |
| CN | 110070576 A | 7/2019 |
| CN | 110085298 A | 8/2019 |
| CN | 110124214 A | 8/2019 |
| CN | 110354406 A | 10/2019 |
| CN | 110368604 A | 10/2019 |
| CN | 110420396 A | 11/2019 |
| CN | 111986777 A * | 11/2020 ............ G06F 30/27 |
| CN | 112546463 A | 3/2021 |
| CN | 113096766 A | 7/2021 |
| CN | 113192554 A | 7/2021 |
| WO | 2018048575 A1 | 3/2018 |

OTHER PUBLICATIONS

Feng, Yongfu et al., Effects of Control Points and Number of Arcs on Dosimetry of Cervical Cancer Radiotherapy Planning, Chinese Medical Equipment Journal, 40(7): 39-43&48, 2019.

* cited by examiner

410

900

```
Obtaining a plurality of training samples, a training
sample including a sample image and a sample         ~ 902
reference image in which a sample dose region is
labeled
              │
              ▼
Generating a dose region prediction model by          ~ 904
training an initial model using the plurality of training
samples
```

1400

SYSTEMS AND METHODS FOR GENERATING TREATMENT PLANS

CROSS-REFERENCE TO RELATED APPLICATIONS

This application claims priority to Chinese Patent Application No. 202110982536.8, filed on Aug. 25, 2021, Chinese Patent Application No. 202110984202.4, filed on Aug. 25, 2021, and Chinese Patent Application No. 202111408059.0, filed on Nov. 24, 2021, the contents of each of which are incorporated herein by reference.

TECHNICAL FIELD

The present disclosure generally relates to radiation therapy, and more particularly to systems and methods for generating treatment plans.

BACKGROUND

Radiation therapy has been widely employed in cancer treatment in which ionizing radiation is guided towards a target region (e.g., a tumor) of a subject (e.g., a patient). In radiation therapy, high-energy electromagnetic radiation beams and/or particles (e.g., alpha rays, beta rays, gamma rays, x-rays, electron rays, proton beams) are delivered for killing or inhibiting the growth of undesired tissue. Generally, the radiation rays need to be delimited so that the radiation dose is maximized in the treatment region and minimized in the healthy tissue of the subject. Therefore, it is desirable to provide systems and methods for generating treatment plans for irradiate the target region to improve the accuracy of the irradiation of the radiation rays.

SUMMARY

In one aspect of the present disclosure, a method for generating a treatment plan for irradiating, using a radiation system, a target region is provided. The method may be implemented on a computing device having at least one processor and at least one storage device. The method may include obtaining at least one parameter from the treatment plan. The at least one parameter may relate to a dose region where is enclosed by an isodose curve. The method may include obtaining an objective function corresponding to the target region. The objective function may represent a conformity between the target region and the dose region. The method may further include generating the treatment plan by optimizing the at least one parameter such that the objective function satisfies an optimization condition.

In some embodiments, the objective function may include at least one of a first conformity parameter or a second conformity parameter. The first conformity parameter may represent a first ratio of a first volume of an intersection region between the target region and the dose region to a second volume of the dose region, and the second conformity parameter may represent a second ratio of the first volume of the intersection region to a third volume of the target region.

In some embodiments, the first volume of the intersection region may be determined by: dividing the target region into a plurality of grid regions; determining a dose of each of the plurality of grid regions of the target region; identifying one or more grid regions from the plurality of grid regions of the target region, wherein for each of the one or more grid regions of the target region, a radiation dose of the grid region satisfies a first dose condition; and determining the first volume of the intersection region based on the one or more grid regions.

In some embodiments, the second volume of the dose region may be determined by: dividing a surface of the subject into a plurality of grid regions; determining a dose of each of the plurality of grid regions of the surface; identifying one or more grid regions from the plurality of grid regions of surface, wherein for each of the one or more grid regions, a radiation dose of the grid region satisfies a second dose condition; and determining the second volume of the dose region based on the one or more grid regions.

In some embodiments, the objective function may correspond to a target dose. The target region may include at least one of a target to be irradiated at the target dose or a low dose region to be irradiated at a dose lower than the target dose.

In some embodiments, the low dose region may include a region that abuts the target. The low dose region may be determined by: obtaining a dose difference between the target dose and the dose of the low dose region; determining, based on the dose difference, a falling distance expanded from a boundary of the target; and adjusting, based on the falling distance, the low dose region.

In some embodiments, the optimization condition may include at least one of a result of the objective function is below an objective function value threshold, or a variation between results of the objective function of a plurality of consecutive iterations of an iterative process for generating the treatment plan is below a variation threshold.

In some embodiments, the determining the at least one parameter such that the objective function satisfies an optimization condition may include obtaining a target image of a subject, the subject including the target region, generating a predicted image based on the target image and a dose region prediction model, and determining the at least one parameter based on the predicted image. The predicted image may include a representation of a prediction of the dose region.

In some embodiments, the dose region prediction model may be generated according to a process including obtaining a plurality of training samples, a training sample including a sample image and a sample reference image in which a sample dose region is labeled, and generating the dose region prediction model by training an initial model using the plurality of training samples.

In some embodiments, the method may further include obtaining a target image of a subject. The subject may include the target region. The method may include determining, based on the target image, a plurality of sampling points in a vicinity of a boundary of the target region. The method may include determining one or more dose control points by using at least one filter to filter the plurality of sampling points. Each of the at least one filter may include a first boundary and a second boundary, and the first boundary may be located inside the second boundary. The method may further include updating, based on the one or more dose control points, the at least one parameter.

In some embodiments, the determining one or more dose control points by using at least one filter to filter the plurality of sampling points may include: for each of the plurality of sampling points, determining a parameter value of at least one contour parameter of the target region between the first boundary and the second boundary corresponding to the sampling point, and determining whether the sampling point is a dose control point based on the parameter value of the at least one contour parameter.

In some embodiments, the method may be implemented by a plurality of graphics processing units (GPUs) in a parallel configuration. The at least one filter may include a plurality of filters, and the plurality of GPUs may be configured to determine the one or more dose control points by using the plurality of filters to filter the plurality of sampling points.

In some embodiments, the method may include verifying the at least one determined parameter of the treatment plan based on a user instruction.

In some embodiments, the method may include causing the radiation system to execute the treatment plan.

In some embodiments, the causing the radiation system to execute the treatment plan may include positioning, based on the treatment plan, a radiation source to deliver at least one radiation beam to the target region.

In some embodiments, the target region may include a plurality of target regions at different target doses. The plurality of target regions may be spatially separate. The plurality of target regions may be designated as a first target region, a second target region, . . . , an $m^{th}$ target region according to corresponding target doses from high to low. The method may further include sequentially adjusting at least one target region from the second target region to the $m^{th}$ target region. For a $j^{th}$ target region among the second target region through the $m^{th}$ target region in which m is an integer greater than or equal to 2, and j is an integer within a range from 2 to m, the method may include determining a dose difference between a $j-1^{th}$ target dose corresponding to a $j-1^{th}$ target region and a $j^{th}$ target dose corresponding to a $j^{th}$ target region; determining, based on the dose difference, a falling distance expanded from a $j-1^{th}$ boundary of the $j-1^{th}$ target region; and adjusting, based on the falling distance and the $j-1^{th}$ target region, the $j^{th}$ target region. The method may also include generating the treatment plan based on at least one adjusted target region and the first target region.

In some embodiments, the adjusting, based on the falling distance and the $j-1^{th}$ target region, the $j^{th}$ target region may include determining, based on the falling distance and the $j-1^{th}$ target region, an extension region corresponding to the $j^{th}$ target region, and determining an adjusted $j^{th}$ target region based on the $j^{th}$ target region and the extension region corresponding to the $j^{th}$ target region.

In another aspect of the present disclosure, a method for generating a treatment plan for irradiating, using a radiation system, a target region is provided. The method may be implemented on a computing device having at least one processor and at least one storage device. The method may include obtaining a target image of a subject. The subject may include the target region. The method may include determining, based on the target image, a plurality of sampling points in a vicinity of a boundary of the target region. The method may also include determining one or more dose control points by using at least one filter to filter the plurality of sampling points. Each of the at least one filter may include a first boundary and a second boundary, and the first boundary may be located inside the second boundary. The method may further include updating, based on the one or more dose control points, at least one parameter from the treatment plan, the at least one parameter relating to a dose region where is enclosed by an isodose curve.

In some embodiments, the updating, based on the one or more dose control points, at least one parameter of the treatment plan may include obtaining an objective function corresponding to the target region, the objective function representing a conformity between the target region and the dose region; and updating the treatment plan by optimizing the at least one parameter such that the objective function satisfies an optimization condition.

In still another aspect of the present disclosure, a system for generating a treatment plan for irradiating, using a radiation system, a target region is provided. The system may include at least one storage device including a set of instructions, and at least one processor configured to communicate with the at least one storage device. When executing the set of instructions, the at least one processor may be configured to direct the system to perform operations. The operations may include obtaining at least one parameter from the treatment plan. The least one parameter may relate to a dose region where is enclosed by an isodose curve. The operations may include obtaining an objective function corresponding to the target region. The objective function may represent a conformity between the target region and the dose region. The operations may further include generating the treatment plan by optimizing the at least one parameter such that the objective function satisfies an optimization condition.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
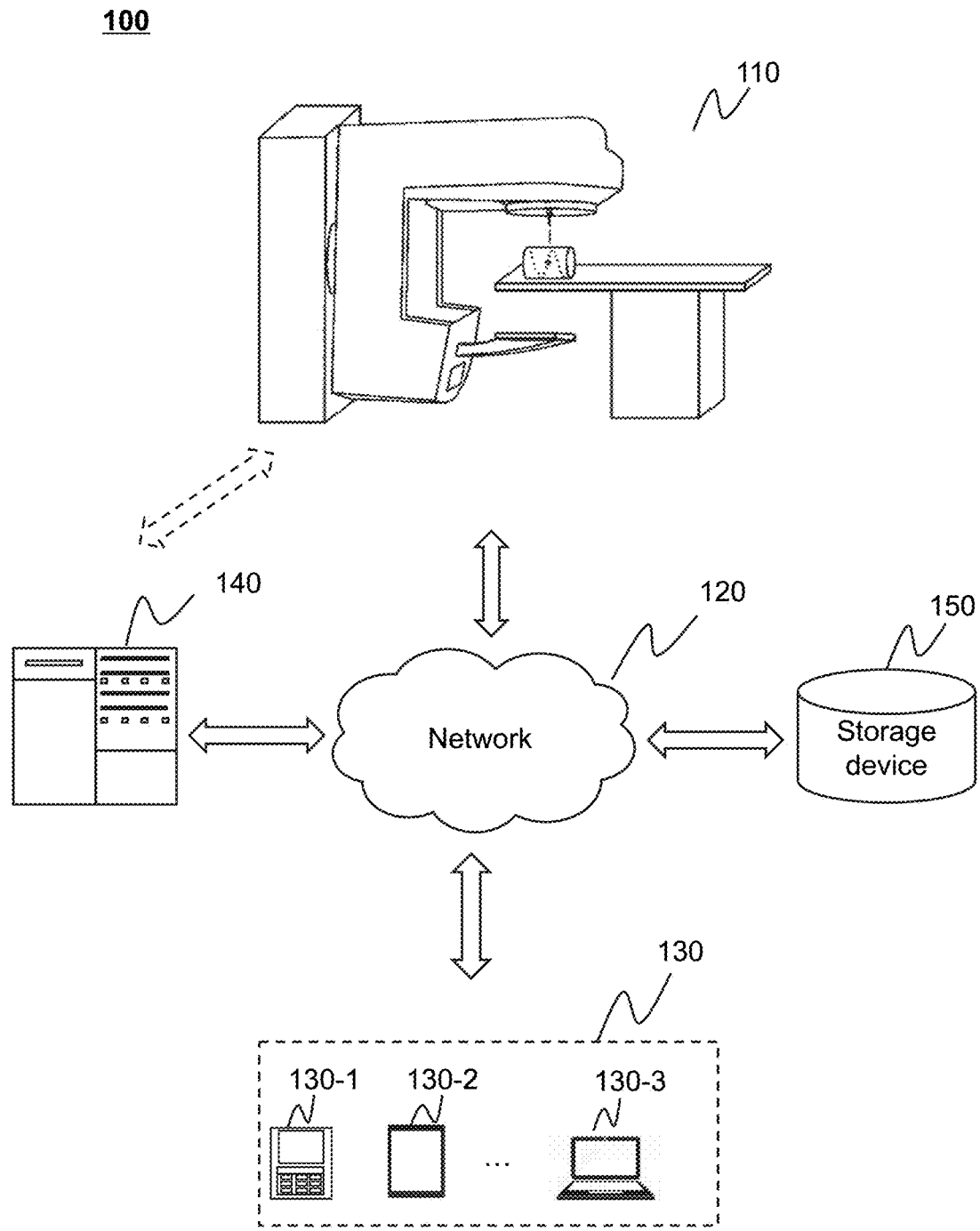
FIG. 1 is a schematic diagram illustrating an exemplary radiation system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof. It will be understood that the term "subject" and "object" may be used interchangeably as a reference to a thing that undergoes a treatment and/or an imaging procedure in a radiation system of the present disclosure.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or synchronously. Moreover, one or more other operations may be added to the flowcharts. One or more operations may be removed from the flowcharts.

In the present disclosure, the term "image" may refer to a two-dimensional (2D) image, a three-dimensional (3D) image, or a four-dimensional (4D) image (e.g., a time series of 3D images). In some embodiments, the term "image" may refer to an image of a region (e.g., a target region, a region of interest (ROI)) of a subject. In some embodiment, the image may be a medical image, an optical image, etc.

In the present disclosure, a representation of a subject (e.g., an object, a patient, or a portion thereof) in an image may be referred to as "subject" for brevity. For instance, a representation of an organ, tissue (e.g., a heart, a liver, a lung), or an ROI in an image may be referred to as the organ, tissue, or ROI, for brevity. Further, an image including a representation of a subject, or a portion thereof, may be referred to as an image of the subject, or a portion thereof, or an image including the subject, or a portion thereof, for brevity. Still further, an operation performed on a representation of a subject, or a portion thereof, in an image may be referred to as an operation performed on the subject, or a portion thereof, for brevity. For instance, a segmentation of a portion of an image including a representation of an ROI from the image may be referred to as a segmentation of the ROI for brevity.

The present disclosure relates to systems and methods for generating a treatment plan for irradiating, using a radiation system, a target region. The methods may include obtaining at least one parameter from the treatment plan. The at least one parameter may relate to a dose region where is enclosed by an isodose curve. The methods may include obtaining an objective function corresponding to the target region. The objective function may represent a conformity between the target region and the dose region. The methods may further include generating the treatment plan by optimizing the at least one parameter such that the objective function satisfies an optimization condition, which in turn may improve the conformity between the target region and the dose region, thereby improving the efficiency and accuracy of the determination of the first shape of the dose region and the treatment plan. Moreover, a machine learning machine (e.g., the dose region prediction model) may be used during the optimization, which may reduce a workload of the user, cross-user variations, and/or dependency on user experience, and improve the efficiency of the optimization process. In addition, one or more dose control points may be determined to locally update the at least one parameter of the treatment plan, which may also improve the efficiency and accuracy of the optimization of the conformity and/or the treatment plan. A treatment plan for a radiotherapy treatment so determined and/or optimized may help improve an accuracy of a radiation delivery to a patient, reduce undesired radiation exposure of the patient, and/or improve the efficacy of the radiotherapy treatment.

FIG. 1 is a schematic diagram illustrating an exemplary radiation system according to some embodiments of the present disclosure. As shown in FIG. 1, the radiation system 100 may include a radiation delivery device 110, a network 120, a terminal device 130, a processing device 140, and a storage device 150. In some embodiments, the radiation delivery device 110, the terminal device 130, the processing device 140, and/or the storage device 150 may be connected to and/or communicate with each other via a wireless connection, a wired connection, or a combination thereof. The components in the radiation system 100 may be connected in one or more of various ways. Merely by way of example, the radiation delivery device 110 may be connected to the processing device 140 directly as indicated by the bi-directional arrow in dotted lines linking the radiation delivery device 110 and the processing device 140. As another example, the radiation delivery device 110 may be connected to the processing device 140 through the network 120. As still another example, the storage device 150 may be connected to the processing device 140 directly or through the network 120. As still another example, the terminal device 130 may be connected to the processing device 140 directly or through the network 120.

In some embodiments, the radiation delivery device 110 may be a radiotherapy (RT) device. In some embodiments, the RT device may deliver one or more radiation beams to a target region (e.g., a tumor) of a subject (e.g., a patient) for causing an alleviation of the subject's symptom. In some embodiments, the RT device may include a conformal radiation therapy device, an image guided radiation therapy (IGRT) device, an intensity modulated radiation therapy (IMRT) device, an intensity modulated arc therapy (IMAT) device, or the like. In some embodiments, the RT device may include a linear accelerator (also referred to as "linac"). The linac may generate and emit a radiation beam (e.g., an X-ray beam) from a treatment head. The radiation beam may pass through one or more collimators (e.g., a multi-leaf collimator (MLC)) forming a certain shape, and enter the subject. In some embodiments, the radiation beam may include electrons, photons, or other types of radiation. In some embodiments, the energy of the radiation beam may be in the megavoltage range (e.g., >1 MeV), referred to as a megavoltage beam. The treatment head may be operably coupled to a gantry. The gantry may rotate, for example, clockwise or counter-clockwise around a gantry rotation axis. In some embodiments, the treatment head may rotate along with the gantry. In some embodiments, the RT device may further include a table configured to transport the subject into and out of the RT device, and/or support the subject during a radiation treatment using the RT device.

In some embodiments, the radiation delivery device 110 may further include one or more multi-leaf collimators (MLCs) (not shown in FIG. 1). The MLC(s) may be configured to collimate radiation beam(s) of the radiation delivery device 110 and/or define the beam shape(s) thereof. In some embodiments, the MLC may include a plurality of leaves. The plurality of leaves may coordinate to form an aperture. The aperture may define or modify the shape of the beam that is delivered to the subject. In some embodiments, one or more leaves of the MLC may be caused to move according to a treatment plan. In some embodiments, the shape of the aperture may be changed according to a desired segment shape of the treatment plan. In some embodiments, the treatment plan may be generated by a treatment planning system (TPS) associated with the radiation system 100. In some embodiments, the treatment plan may include information associated with radiation therapy including, for example, one or more radiation parameters, a treatment dose, or the like, or any combination thereof. The radiation parameters may include at least one parameter of a radiation beam parameter (e.g., the shape of the beam, the shape of the aperture, an intensity, a radiation direction, or the like), a position and/or posture of a subject to be treated, a position of a target region of the subject to be treated, a geometric parameter of the MLC, or the like.

In some embodiments, the radiation delivery device 110 may further include a drive mechanism (not shown in FIG. 1) configured to drive the leaves to move. In some embodiments, the drive mechanism may include one or more driving circuits (not shown in FIG. 1). In some embodiments, a driving circuit may generate driving signal(s) to drive the leaves of the MLC to move towards target position (s) during a treatment. In some embodiments, the driving circuit may be set in the radiation delivery device 110. The driving circuit may communicate with the processing device 140 via, e.g., a connection between the radiation delivery device 110 and the processing device 140. For example, the processing device 140 may provide (or send) a control signal to the drive circuit, and accordingly, the drive circuit may generate a driving signal to cause, e.g., one or more actuators to drive the leaves to move towards their respective target positions.

In some embodiments, the subject to be treated or scanned (also referred to as imaged) may include a body, substance, or the like, or any combination thereof. In some embodiments, the subject may include a specific portion of a body, such as the head, the thorax, the abdomen, or the like, or any combination thereof. In some embodiments, the subject may include a specific organ, such as a breast, the esophagus, a trachea, a bronchus, the stomach, the gallbladder, a small intestine, the colon, the bladder, a ureter, the uterus, a fallopian tube, etc.

The network 120 may include any suitable network that can facilitate exchange of information and/or data for the radiation system 100. In some embodiments, one or more components of the radiation system 100 (e.g., the radiation delivery device 110, the terminal device 130, the processing device 140, the storage device 150, etc.) may communicate information and/or data with one or more other components of the radiation system 100 via the network 120. For example, the processing device 140 may obtain data corresponding to the treatment plan from the radiation delivery device 110 via the network 120. As another example, the processing device 140 may obtain user instructions from the terminal device 130 via the network 120. In some embodiments, the network 120 may include one or more network access points. For example, the network 120 may include wired and/or wireless network access points such as base stations and/or internet exchange points through which one or more components of the radiation system 100 may be connected to the network 120 to exchange data and/or information.

The terminal device 130 may enable interactions between a user and the radiation system 100. The terminal device 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the terminal device 130 may be part of the processing device 140. In some embodiments, the terminal device 130 may remotely operate the radiation delivery device 110. In some embodiments, the terminal device 130 may operate the radiation delivery device 110 via a wireless connection. In some embodiments, the terminal device 130 may receive information and/or instructions inputted by a user, and send the received information and/or instructions to the radiation delivery device 110 or the processing device 140 via the network 120. In some embodiments, the terminal device 130 may receive data and/or information from the processing device 140. In some embodiments, the terminal device 130 may be omitted. In some embodiments, the terminal device 130 may include a control handle, a control box, a console, etc.

The processing device 140 may process data and/or information obtained from the radiation delivery device 110, the terminal device 130, and/or the storage device 150. For example, the processing device 140 may obtain at least one parameter from a treatment plan (e.g., a preliminary treatment plan before an optimization is performed). The least one parameter may relate to a dose region where is enclosed by an isodose curve. As another example, the processing device 140 may obtain an objective function corresponding to the target region. The objective function may represent a conformity between the target region and the dose region. As a further example, the processing device 140 may generate the treatment plan by optimizing the at least one parameter such that the objective function satisfies an optimization condition. As still another example, the processing device 140 may cause the radiation system 100 to execute the treatment plan.

In some embodiments, the processing device 140 may be a computer, a user console, a single server or a server group, etc. The server group may be centralized or distributed. In some embodiments, the processing device 140 may be local or remote. For example, the processing device 140 may access information and/or data stored in the radiation delivery device 110, the terminal device 130, and/or the storage device 150 via the network 120. As another example, the processing device 140 may be directly connected to the radiation delivery device 110, the terminal device 130, and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the processing device 140 may be implemented by a computing device. For example, the computing device may include a processor, a storage, an input/output (I/O), and a communication port. The processor may execute computer instructions (e.g., program codes) and perform functions of the processing device 140 in accordance with the techniques described herein. The computer instructions may include, for example, routines, programs, objects, components, data structures, procedures, modules, and functions, which perform particular functions described herein. In some embodiments, the processing device 140, or a portion of the processing device 140 may be implemented by a portion of the terminal device 130.

In some embodiments, the processing device 140 may include multiple processing devices. Thus operations and/or method steps that are performed by one processing device as described in the present disclosure may also be jointly or separately performed by the multiple processing devices. For example, if in the present disclosure the, the radiation system 100 executes both operation A and operation B, it should be understood that operation A and operation B may also be performed by two or more different processing devices jointly or separately (e.g., a first processing device executes operation A and a second processing device executes operation B, or the first and second processing devices jointly execute operations A and B).

The storage device 150 may store data, instructions, and/or any other information. In some embodiments, the storage device 150 may store data obtained from the radiation delivery device 110, the terminal device 130 and/or the processing device 140. For example, the storage device 150 may store the at least one parameter from the treatment plan, the objective function corresponding to the target region, etc. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the radiation system 100 (e.g., the processing device 140, the terminal device 130, etc.). One or more components in the radiation system 100 may access the data or instructions stored in the storage device 150 via the network 120. In some embodiments, the storage device 150 may be directly connected to or communicate with one or more other components in the radiation system 100 (e.g., the processing device 140, the terminal device 130, etc.). In some embodiments, the storage device 150 may be part of the processing device 140. In some embodiments, the processing device 140 may be connected to or communicate with the radiation delivery device 110 via the network 120, or at the backend of the processing device 140.

Figure 2:
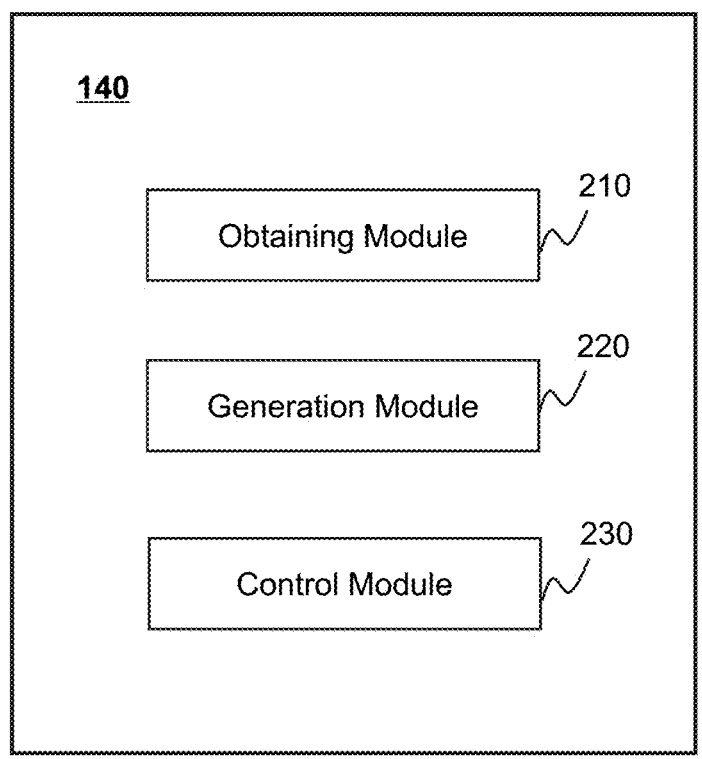
FIG. 2 is a block diagram illustrating an exemplary processing device according to some embodiments of the present disclosure.

FIG. 2 is a block diagram illustrating an exemplary processing device according to some embodiments of the present disclosure. In some embodiments, the modules illustrated in FIG. 2 may be implemented on a computing device. In some embodiments, the processing device 140 may include an obtaining module 210, a generation module 220, and a control module 230.

The obtaining module 210 may be configured to obtain at least one parameter from the treatment plan. The at least one parameter may relate to a dose region where is enclosed by an isodose curve. The obtaining module 210 may be configured to obtain an objective function corresponding to the target region. The objective function may represent a conformity between the target region and the dose region. More descriptions regarding the obtaining of the at least one parameter and the objective function may be found elsewhere in the present disclosure (e.g., FIGS. 3-14 and relevant descriptions thereof).

The generation module 220 may be configured to generate the treatment plan by optimizing the at least one parameter such that the objective function satisfies an optimization condition. More descriptions regarding the generation of the treatment plan may be found elsewhere in the present disclosure (e.g., FIGS. 3-14 and relevant descriptions thereof).

The control module 230 may be configured to cause a radiation system to execute the treatment plan. More descriptions regarding the control of the radiation system may be found elsewhere in the present disclosure (e.g., FIGS. 3-14 and relevant descriptions thereof).

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof.

It should be noted that the above descriptions of the processing device 140 are provided for the purposes of illustration, and are not intended to limit the scope of the present disclosure. For persons having ordinary skills in the art, various variations and modifications may be conducted under the guidance of the present disclosure. However, those variations and modifications do not depart from the scope of the present disclosure. In some embodiments, the processing device 140 may include one or more other modules. For example, the processing device 140 may include a storage module used to store data generated by the modules in the processing device 140. In some embodiments, two or more of the modules may be combined as a single module, and any one of the modules may be divided into two or more units.

Figure 3:
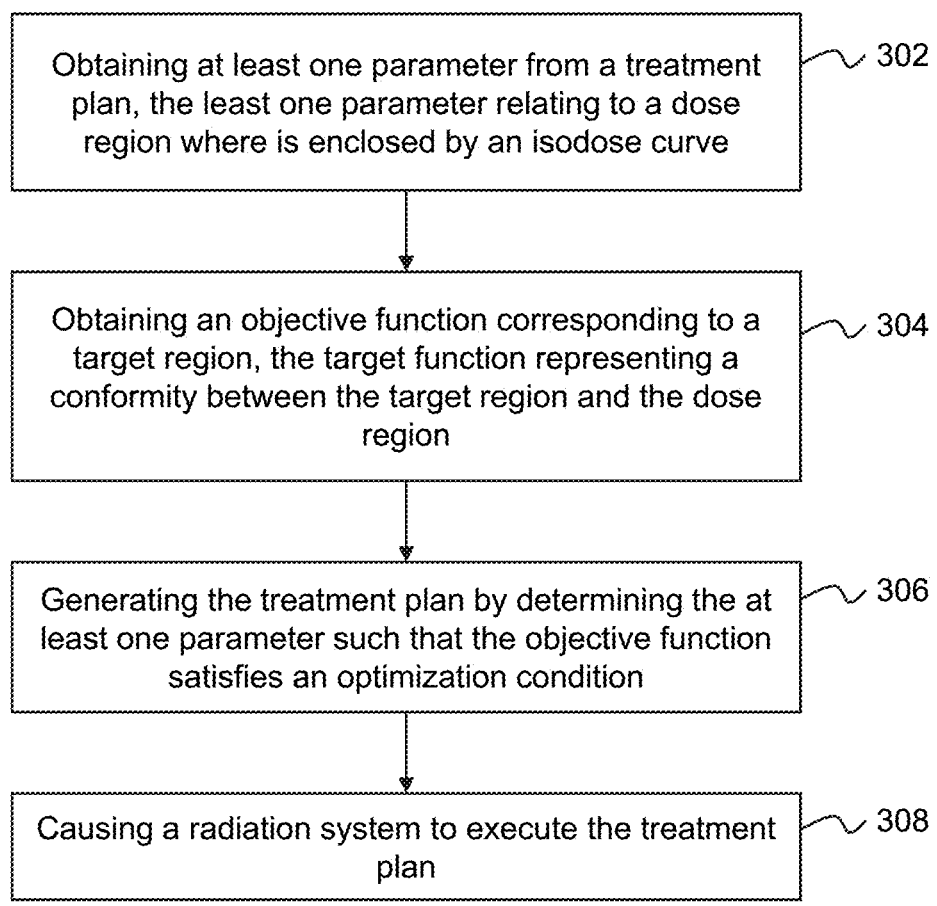
FIG. 3 is a flowchart illustrating an exemplary process for generating a treatment plan according to some embodiments of the present disclosure.

FIG. 3 is a flowchart illustrating an exemplary process 300 for generating a treatment plan according to some embodiments of the present disclosure. In some embodiments, process 300 may be executed by the radiation system 100. For example, the process 300 may be stored in the storage device 150 in the form of instructions (e.g., an application), and invoked and/or executed by the processing device 140. The operations of the illustrated process presented below are intended to be illustrative. In some embodiments, the process 300 may be accomplished with one or more additional operations not described, and/or without one or more of the operations discussed. Additionally, the order in which the operations of the process 300 as illustrated in FIG. 3 and described below is not intended to be limiting.

In radiation therapy, radiation rays need to be delimited so that a radiation dose (or referred to as dose for brevity) in a target region is higher than in healthy tissue of a subject. Therefore, a treatment plan may need to be determined. Conventionally, the treatment plan may be determined manually. For example, a user (e.g., a doctor, a physician, a technician) may segment tumor(s) and/or organ(s) from an image of a subject, and determine and/or optimize a treatment plan based on a segmentation result (e.g., a gross tumor volume (GTV), a clinical target volume (CTV), and/or a planning target volume (PTV)). For determining the treatment plan, the user may pay attention to dose indicators, e.g., whether a dose in a target region reaches a predetermined dose (e.g., a radiation dose in 95% of a volume of a target region D95), an average dose of an organ at risk (OAR), a conformity between a dose region and a target region, etc., so as to optimize the treatment plan.

In some embodiments, the treatment plan may be determined/optimized by improving the conformity between the dose region and the target region. As an example, to improve the conformity, a ring may be manually drawn on a planning image that includes a representation of the target region. For instance, after a user delineates a target region in the planning image by drawing a segmentation line, the user may draw a ring by expanding the segmentation line, and determine a constraint (e.g., a dose, a volume) for the ring. As another example, a falling function may be determined to improve the conformity. For instance, a dose in a vicinity of the target region may be determined according to a falling function and a dose of the target region, thereby improving the accuracy of the dose in the vicinity of the target region. However, before the ring is manually drawn, the segmentation line of the target region needs to be manually determined, which is troublesome, and the quality of the segmentation line depends on factors including, e.g., user experience. Further, the constraint corresponding to the ring may be inappropriate, which may adversely affect the dose of the target region, and reduce the conformity. Whether the conformity may be improved based on the falling function may depend on a specific design and/or parameter(s) of the falling function, the effect of which on improving the conformity and/or the treatment plan may be indirect or obscure. The process 300 may be performed to improve the treatment plan by directly and automatically improving the conformity.

In 302, the processing device 140 (e.g., the obtaining module 210) may obtain at least one parameter from a treatment plan (e.g., a preliminary treatment plan before an optimization according to embodiments of the present disclosure is performed).

The at least one parameter may relate to a dose region where a target region is enclosed by an isodose curve. The isodose curve may refer to a curve that points on the curve correspond to a same dose. In some embodiments, the at least one parameter may include a shape of radiation beam (s), a shape of an aperture formed by an MLC, a radiation direction, or the like. For example, the first shape of the dose region may be adjusted based on the at least one parameter.

In some embodiments, the processing device 140 may obtain the at least one parameter from the treatment plan. For example, after a treatment plan is generated by a TPS associated with the radiation system 100, the processing device 140 may obtain the treatment plan from the TPS or a storage device (e.g., the storage device 150, a database, or an external storage device) that stores the treatment plan, and further obtain the at least one parameter from the treatment plan.

Figure 4:
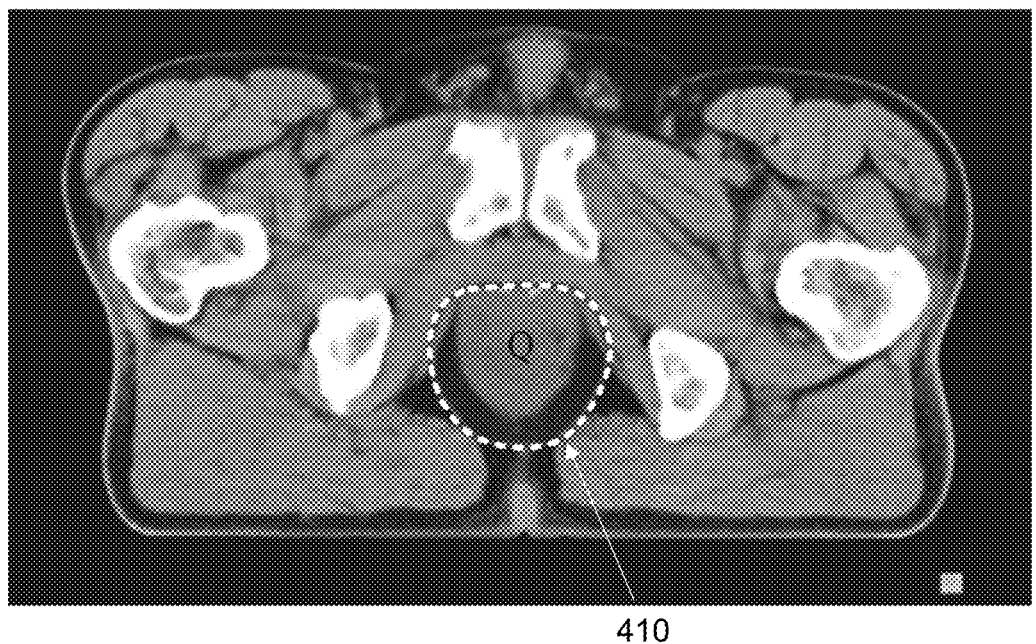
FIG. 4 is a schematic diagram illustrating an exemplary image of a subject according to some embodiments of the present disclosure.

In some embodiments, the dose region may correspond to a target region. The target region may include a region of a subject that needs to be treated or diagnosed. For example, the target region may include at least part of a malignant tissue (e.g., a tumor, a cancer-ridden organ, a non-cancerous target of radiation therapy). Merely by way of example, the target region may include a lesion (e.g., a tumor, a lump of abnormal tissue), an organ with a lesion, a tissue with a lesion, or any combination thereof. As another example, as illustrated in FIG. 4, a target region 410 may be segmented from an image (e.g., a planning image) of a subject.

In some embodiments, the target region may be determined manually and/or automatically based on an image (e.g., a planning image) of the subject. Merely by way of example, the image of the subject may be displayed on a user interface of the TPS, and the target region may be segmented manually and/or automatically. For example, a user may determine (e.g., by drawing a boundary of) the target region on the image of the subject. As another example, the target region may be obtained by segmenting, by a processing device of the TPS, the image of the subject using an image segmentation model. As still another example, after the image of the subject is segmented by a processing device of the TPS using the image segmentation model, the user may check and/or revise the target region marked on the image of the subject.

Figure 7:
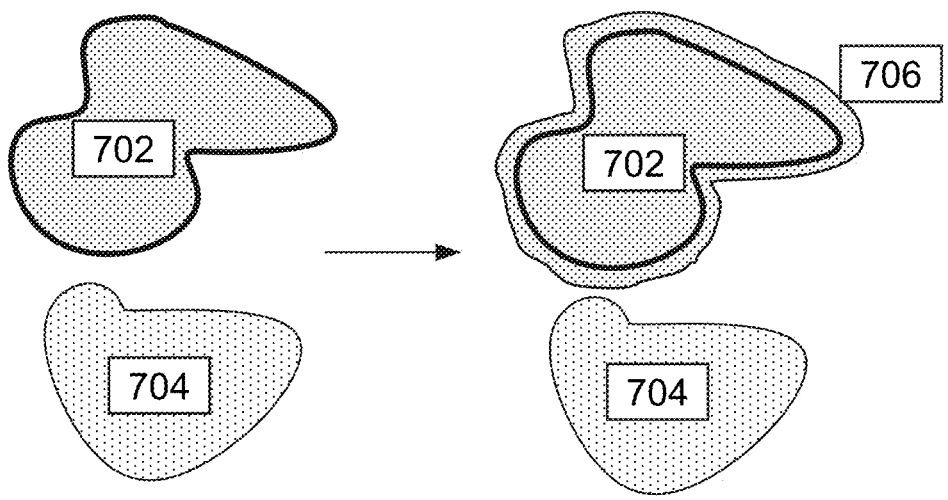
FIG. 7 is a flowchart illustrating an exemplary process for adjusting a target region according to some embodiments of the present disclosure.

In some embodiments, a plurality of target regions may be determined based on the image of the subject. For example, as illustrated in FIG. 7, a subject may include a first target region 702 and a second target region 704. In some embodiments, radiation doses of the plurality of target regions may be the same or different. For example, as illustrated in FIG. 7, a first dose corresponding to the first target region 702 may be the same as or different from a second dose corresponding to the second target region 704.

In some embodiments, the image may include a medical image including anatomical information of the subject. Exemplary images may include a CT image, an MR image, a PET image, an X-ray image, an ultrasound image, or the like. In some embodiments, the image may be a 3-dimensional image including a stack of slices. In some embodiments, the processing device 140 may obtain the image from a medical imaging device or a storage device (e.g., the storage device 150, a database, or an external storage device) that stores the image of the subject.

In 304, the processing device 140 (e.g., the obtaining module 210) may obtain an objective function corresponding to the target region. The objective function may represent a conformity between the target region and the dose region.

The conformity may refer to a similarity degree between the target region and the dose region. For example, the conformity between the target region and the dose region may include a similarity degree between a second shape of the target region and a first shape of the dose region, a similarity degree between a volume (i.e., the third volume) of the target region and a volume (i.e., the second volume) of the dose region, etc. In some embodiments, the conformity may be represented by a conformity index. The conformity index may be defined as a ratio of a square of a second volume of the target region enclosed by an isodose volume (e.g., a 100% isodose volume) to a multiplication of a third volume of the target region with the isodose volume. As used herein, the isodose volume may be a volume formed by the isodose curve (e.g., a 100% isodose curve). For example, an isodose curve may define a certain volume of the subject (e.g., the target region), and the certain volume may be designated as the isodose volume. The conformity may be expressed using a positive number smaller than or equal to 1. In some embodiments, the higher the conformity, the higher the similarity degree. When the conformity is 1, the second shape of the target region may be the same as the first shape of the dose region, indicating that the dose region completely coincides with the target region.

In some embodiments, the objective function may include at least one of a first conformity parameter or a second conformity parameter. The first conformity parameter may represent a first ratio of a first volume of an intersection region between the target region and the dose region to a second volume of the dose region. In some embodiments, the first conformity parameter may refer to an extent of coverage of the target region by the dose region. Merely by way of example, a first conformity parameter of a target region may be determined based on Equation $$F = \frac{TV\_RI}{V\_RI}, \tag{1}$$

where F represents the first conformity parameter of the target region, TV_RI represents a first volume of an intersection region between the target region and a corresponding dose region, and TV_RI represents a second volume of the corresponding dose region.

The second conformity parameter may represent a second ratio of the first volume of the intersection region to a third volume of the target region. In some embodiments, the second conformity parameter may refer to an extent of overlapping of the target region with the dose region. Merely by way of example, a second conformity parameter of the target region may be determined based on Equation (2):

$$S = \frac{TV\_RI}{TV}, \tag{2}$$

where S represents a second conformity parameter of the target region, and TV represents a third volume of the target region.

In some embodiments, the processing device 140 may determine the first conformity parameter based on the first volume of the intersection region between the target region and the dose region and the second volume of the dose region. In some embodiments, the first volume of the intersection region may be determined by dividing the target region into a plurality of grid regions, determining a dose of each of the plurality of grid regions of the target region, identifying one or more grid regions from the plurality of grid regions of the target region, and determining the first volume of the intersection region based on the identified one or more grid regions. In some embodiments, the processing device 140 may obtain a first 3D model corresponding to the target region, and divide the first 3D model corresponding to the target region into the plurality of grid regions. The first 3D model may represent a morphology of the target region. Exemplary first 3D models may include a mesh model (e.g., a human mesh model), a 3D mask, a kinematic model, or the like, or any combination thereof. For example, the processing device 140 may establish a first 3D model corresponding to a target region based on an image of a subject and a treatment plan (e.g., positional information and/or anatomical information regarding the target region in the treatment plan). As another example, a first 3D model corresponding to a target region may be pre-established and stored in a storage device (e.g., the storage device 150, a database, or an external storage device), and the processing device 140 may obtain the first 3D model from the storage device. In some embodiments, the processing device 140 may identify the one or more grid regions from the plurality of grid regions of the target region by determining whether a radiation dose of the grid region satisfies a first dose condition. In some embodiments, the first dose condition may include that the radiation dose of the grid region exceeds or reaches a target dose. The target dose may be determined based on the treatment plan. The processing device 140 may deem that the identified one or more grid regions of the target region belong to the intersection region. Accordingly, the processing device 140 may determine the first volume of the intersection region based on the identified one or more grid regions and grid volume(s) of the corresponding grid region (s). In some embodiments, a grid volume of each grid region in the plurality of grid regions may be determined based on a system default setting or set manually by a user. For example, the processing device 140 may designate a volume (e.g., 1×1×1 millimeter$^3$) as a grid volume of each grid region based on a user instruction. If the grid volume of each grid region is the same, the processing device 140 may determine the first volume of the intersection region by counting the number of the identified one or more grid regions of the target region, and multiplying the number (or count) of the identified one or more grid regions with the grid volume of each grid region. If grid volumes of the plurality of grid regions are different, the processing device 140 may determine the first volume of the intersection region by summing up grid volumes of the identified one or more grid regions.

In some embodiments, the second volume of the dose region may be determined by dividing a surface of the subject into a plurality of grid regions, determining a dose of each of the plurality of grid regions of the surface, identifying one or more grid regions from the plurality of grid regions of the surface, and determining the second volume of the dose region based on the identified one or more grid regions. In some embodiments, the processing device 140 may obtain a second 3D model corresponding to the subject, and divide the second 3D model corresponding to the dose region into the plurality of grid regions. The second 3D model may represent a structure of the subject. The obtaining of the second 3D model may be similar to the obtaining of the first 3D model, which is not repeated. In some embodiments, the processing device 140 may identify the one or more grid regions from the plurality of grid regions of the surface by determining whether a radiation dose of the grid region satisfies a second dose condition. In some embodiments, the second dose condition may be the same as or different from the first dose condition. Accordingly, the determination of the second volume may be similar to the determination of the first volume, which is not repeated.

In some embodiments, the processing device 140 may determine the second conformity parameter based on the first volume of the intersection region and the third volume of the target region. In some embodiments, the third volume of the target region may be determined by dividing the target region into a plurality of grid regions, determining a grid volume of each of the plurality of grid regions of the target region, and determining the third volume of the target region by summing up the grid volume of each of the plurality of grid regions.

In some embodiments, the grid volume of each grid region of a specific region is (substantially) the same, and the volume (e.g., the first volume, the second volume, the third volume) of the region may be determined based on a count of grid regions that are deemed belonging to the region (e.g., a grid region that is deemed belonging to the intersection region, a grid region that is deemed belonging to the dose region, a grid region that is deemed belonging to the target region), which may simplify the process of and therefore improve the efficiency of the determination of the volume of a region. As used herein, substantially, when used to qualify a feature (e.g., equivalent to, same), indicates that the deviation from the feature is below a threshold, e.g., 30%, 25%, 20%, 15%, 10%, 5%, etc.

In some embodiments, the processing device 140 may obtain the objective function corresponding to the target region based on the first conformity parameter and/or the second conformity parameter. For example, an objective function corresponding to a target region may be determined according to Equation (3):

$$f_C = F \times S = \frac{\text{TV\_RI} \times \text{TV\_RI}}{\text{V\_RI} \times TV}, \quad (3)$$

where $f_C$ represents a result (or a value) of the objective function corresponding to the target region.

In some embodiments, a result of $f_C$ may be within a range from 0 to 1, wherein the larger the result of $f_C$, the larger the conformity. When the result of $f_C$ is 1, the conformity may be largest, and the second shape of the target region may be the same as the first shape of the dose region.

In some embodiments, when the subject includes a plurality of target regions, the processing device 140 may obtain the objective function based on the plurality of target regions. Merely by way of example, for an $i^{th}$ target region among N target regions, the processing device 140 may determine a first conformity parameter and a second conformity parameter according to Equation (4) and Equation (5), respectively:

$$F_I = \frac{TV\_RI_I}{V\_RI_I}, \quad (4)$$

$$S_I = \frac{TV\_RI_I}{TV_I}, \quad (5)$$

where I represents the $I^{th}$ target region, $F_I$ represents the first conformity parameter corresponding to the $I^{th}$ target region, $TV\_RI_I$ represents a first volume of an intersection region between the $I^{th}$ target region and an $I^{th}$ dose region corresponding to the $I^{th}$ target region, $V\_RI_I$ represents a second volume of the $I^{th}$ dose region, $S_I$ represents the second conformity parameter corresponding to the $I^{th}$ target region, $TV_I$ represents a third volume of the $I^{th}$ target region, N is a positive integer, and I is a positive integer within a range from 1 to N.

Further, the processing device 140 may obtain the objective function based on the first conformity parameter and the second conformity parameter corresponding to the $I^{th}$ target region. For example, the objective function corresponding to the N target regions may be determined according to Equation (6):

$$f_{obj}{}^N = \Sigma_{I=1}{}^{I=N}[w_I(f_{CI} - C_{index})^2], \quad (6)$$

where $w_I$ represents a weight of the importance of the $I^{th}$ target region on the N target regions, $f_{obj}{}^N$ represents a result of the objective function corresponding to the N target regions, $f_{CI} = F_I S_I$ that represents a product of the first conformity parameter and the second conformity parameter corresponding to the $I^{th}$ target region, and $C_{index}$ represents a preset constant. Merely by way of example, considering that the conformity is largest when the result of $f_{CI}$ is 1, a value of $C_{index}$ may be determined to be 1, which is not intended to be limiting.

In some embodiments, $f_{obj}{}^N$ may be used to characterize a similarity degree between the result of $f_{CI}$ and the value of $C_{index}$. The less a result of $f_{obj}{}^N$, the larger the similarity degree between the result of $f_{CI}$ and the value of $C_{index}$. When the result of $f_{obj}{}^N$ is equal to 0, the result of $f_{CI}$ may be the same as the value of $C_{index}$, and the conformity may be largest. That is, a second shape of each of the plurality of target regions may be the same as a first shape of a corresponding dose region of the plurality of dose regions.

In some embodiments, the effect of the first conformity parameter on the objective function may be different from the effect of the second conformity parameter on the objective function. Accordingly, the processing device 140 may assign different weights to the first conformity parameter and the second conformity parameter, respectively. Merely by way of example, the objective function corresponding to the N target regions may be determined according to Equation (7):

$$f_{obj}{}^N = \Sigma_{I=1}{}^{I=N}[w_{1I}(F_I - C_{index1})^2 + w_{2I}(S_I - C_{index2})^2], \quad (7)$$

where $w_{1I}$ represents a weight of the first conformity parameter, $w_{2I}$ represents a weight of the second conformity parameter, $C_{index1}$ represents a preset constant corresponding to the first conformity parameter $F_I$, and $C_{index2}$ represents a preset constant corresponding to the second conformity parameter $S_I$. Merely by way of example, considering that the conformity is largest when the result of $F_I$ is 1, a value of $C_{index1}$ may be determined to be 1; similarly, a value of $C_{index2}$ may be determined to be 1, which is not intended to be limiting.

In some embodiments, $f_{obj}{}^N$ may be used to characterize a first similarity degree between the result of $F_1$ and the value of $C_{index1}$ and a second similarity degree between the result of $S_I$ and the value of $C_{index2}$. The less a result of $f_{obj}{}^N$, the larger the first similarity degree between the result of $F_1$ and the value of $C_{index1}$ and the second similarity degree between the result of $S_I$ and the value of $C_{index2}$. When the result of $f_{obj}{}^N$ is equal to 0, the result of $F_1$ may be the same as the value of $C_{index1}$, and the result of $S_I$ may be the same as the value of $C_{index2}$. At this time, the conformity may be the largest. That is, a second shape of each of the plurality of target regions may be the same as a first shape of each of the plurality of target regions.

In some embodiments, the processing device 140 may adjust $w_{1I}$ and $w_{2I}$ based on actual situations. For example, when a subject is a patient with a breast cancer, the processing device 140 may reduce a value of $w_{2I}$, which may reduce the extent of overlapping between the target region and the dose region and maintain the extent of coverage of the target region by the dose region. That is, the second similarity may be reduced such that the first similarity degree between the result of $F_1$ and the value of $C_{index1}$ is larger than the second similarity degree between the result of $S_I$ and the value of $C_{index2}$. Therefore, a difference between the target region and the intersection region may be larger than a difference between the dose region and the intersection region. In other words, the dose region may fall within the target region. Accordingly, a dose to OARs in the vicinity of but outside the target region may be reduced. As another example, the processing device 140 may reduce a value of $w_{1I}$, which may reduce the extent of coverage of the target region by the dose region and maintain a value of $w_{2I}$, the extent of overlapping between the target region to the dose region. That is, the first similarity may be reduced such that the first similarity degree between the result of $F_1$ and the value of $C_{index1}$ is less than the second similarity degree the result of $S_1$ and the value of $C_{index2}$. Therefore, a difference between the target region and the intersection region may be less than a difference between the dose region and the intersection region. In other words, the target region may fall within the dose region. Accordingly, a dose to the target region may be ensured.

By adjusting $w_{1I}$ corresponding to the first conformity parameter and $w_{2I}$ corresponding to the second conformity parameter, the objective function may be adjusted based on actual situations, allowing flexibility in the objective function, which may improve the efficiency and adaptability of the optimization to various situations, and the efficacy of the treatment plan so determined/optimized.

In some embodiments, the objective function may correspond to a plurality of target regions, and doses of the plurality of target regions may be different. For example, the target region may include a target to be irradiated at the target dose and a low dose region to be irradiated at a dose lower than the target dose, wherein the low dose region may include a region that abuts the target. In some embodiments, the processing device 140 may adjust the low dose region. For example, the processing device 140 may obtain a dose difference between the target dose and the dose of the low dose region, determine a falling distance from a boundary of the target based on the dose difference, and adjust the low dose region based on the falling distance. Further, the processing device 140 may determine the objective function based on the target and the determined low dose region. More descriptions regarding the determination of the objective function may be found elsewhere in the present disclosure (e.g., FIGS. 6-7 and the descriptions thereof).

In 306, the processing device 140 (e.g., the generation module 220) may generate the treatment plan by optimizing the at least one parameter such that the objective function satisfies an optimization condition.

Since the at least one parameter relates to the first shape of the dose region, the first shape of the dose region may change with the optimization of the at least one parameter. Accordingly, the first volume of the intersection region (e.g., TV_RI, TV_RI$_f$) and the second volume of the dose region (e.g., V_RI, V_RI$_f$) that relate to the first shape may change with the optimization of the at least one parameter.

In some embodiments, the processing device 140 may optimize the at least one parameter using an optimization algorithm. Exemplary optimization algorithms may include a simulated annealing algorithm, a gradient algorithm, an ant colony algorithm, or the like, or any combination thereof. Merely by way of example, the processing device 140 may optimize the at least one parameter in an iterative process including a plurality of iterations such that the objective function satisfies the optimization condition. The optimization condition may refer to a termination condition for optimizing the at least one parameter. It should be noted that the result of the target result may be a certain value larger than 0. In some embodiments, the optimization condition may include that the result of the objective function is below an objective function value threshold, a variation between results of the objective function of a plurality of consecutive iterations of the iterative process for optimizing the at least one parameter is below a variation threshold, or the like, or any combination thereof. The objective function value threshold or the variation threshold may be determined based on a system default setting or set manually by the user, such as, 0.3, 0.2, 0.1, 0.05, 0.01, etc.

Merely by way of example, the processing device 140 may optimize the at least one parameter using the gradient algorithm such that the objective function (e.g., Equation (6)) satisfies the optimization condition. Taking an objective function corresponding to one target region as an example (i.e., I or N is 1), the objective function corresponding to the target region may be determined according to Equation (8):

$$f_{obj}^1 = w_1(f_{C1} - C_{index})^2, \quad (8)$$

where $f_{obj}^1$ represents the objective function of the target region, $w_1$ represents a weight indicating the impact of the target region on the value of the objective function $f_{obj}^1$, and $f_{C1}$ represents a product of the first conformity parameter and the second conformity parameter corresponding to the target region.

Figure 5:
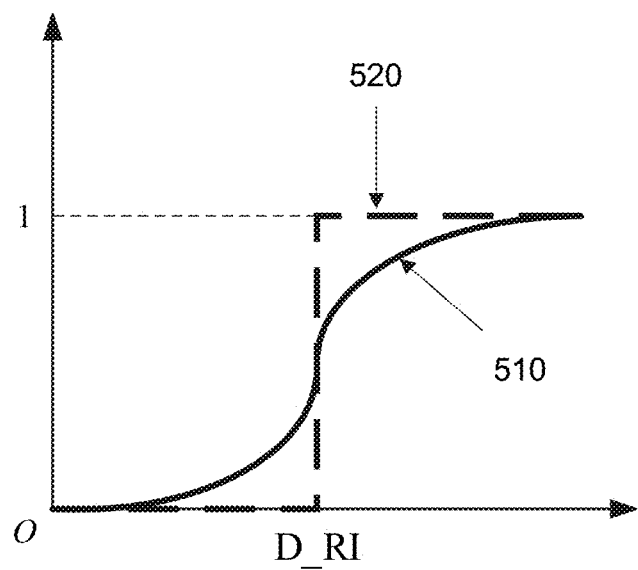
FIG. 5 is a schematic diagram illustrating an exemplary sigmoid function according to some embodiments of the present disclosure.

Since the volume (e.g., the first volume, the second volume, the third volume) may be determined based on the count of grid regions that belong to the volume, each of the plurality of grid regions may be represented by a value "0" and a value "1." The value "0" may represent that the grid region is outside a volume and therefore not counted (e.g., the radiation dose of the grid region failing to satisfy the first dose condition, the radiation dose of the grid region failing to satisfy the second dose condition) for determining the volume; the value "1" may represent that the grid region is within a volume and needs to be counted for determining the volume (e.g., the radiation dose of the grid region satisfying the first dose condition, the radiation dose of the grid region satisfying the second dose condition). In some embodiments, a unit step function of "0-1" may be approximated with a function, e.g., a sigmoid function, that has a finite and/or continuous derivative. See, e.g., FIG. 5 illustrating an exemplary sigmoid function according to some embodiments of the present disclosure. As shown in FIG. 5, a solid line 510 representing a sigmoid function may replace a dotted line 520 representing the unit step function of "0-1." The sigmoid function $f_{sigmoid}$ may be represented according to Equation (9):

$$f_{sigmoid} = \frac{1}{1+e^{-x}}, \quad (9)$$

where x represents a target dose, and e represents the natural constant.

In some embodiments, $f_{sigmoid}$ may be a value within a range from 0 to 1.

A derivative of the sigmoid function may be represented according to Equation (10):

$$f_{der-sigmoid} = f_{sigmoid} \times (1 - f_{sigmoid}), \quad (10)$$

For an $i^{th}$ grid region among the plurality of grid regions in the target region, a gradient with respect to the $i^{th}$ grid region may be determined according to Equation (11):

$$Grad_{k1} = \frac{\begin{array}{c} 2 \times w_1 \times (f_{C1} - C_{index}) \times \\ \left[ 2 \times TV\_RI \times V\_RI \times f_{der-sigmoid}\left(d_{diff}^{k1}\right) \times \right. \\ \left. V_{ptv-i} - TV\_RI \times TV\_RI \times f_{der-sigmoid}\left(d_{diff}^{k1}\right) \times V_{i-ext} \right] \end{array}}{(V\_RI \times V\_RI)}, \quad (11)$$

where i represents an $i^{th}$ grid region, $V_{ptv-i}$ represents a ratio of a volume of the target region to a volume of the $i^{th}$ grid region, $V_{i-ext}$ represents a ratio of a volume of the target region to a volume of the dose region, k1 represents a dose of the $i^{th}$ grid region in the target region, and $d_{diff}^{k1}$ represents a difference between k1 and the target dose.

For an $i^{th}$ grid region among the plurality of grid regions in the dose region, a gradient with respect to the $i^{th}$ grid region may be determined according to Equation (12):

$$Grad_{k2} = \frac{-2 \times w_1 \times (f_{C1} - C_{index}) \times }{V\_RI \times V\_RI} TV\_RI \times TV\_RI \times f_{der-sigmoid}\left(d_{diff}^{k2}\right) \times V_{ext-i}, \quad (12)$$

where $V_{ext-i}$ represents a ratio of a volume of the dose region to a volume of the $i^{th}$ grid region, k2 represents a dose of the $i^{th}$ grid region in the dose region, and $d_{diff}^{k2}$ represents a difference between k2 and the target dose.

It should be noted that since an order of magnitudes of at least one of $d_{diff}^{k1}$ or $d_{diff}^{k2}$ is ±10$^3$, and a range of a result corresponding to the sigmoid function $f_{sigmoid}$ (e.g., $e^{-x}$) is limited, $d_{diff}^{k1}$ and/or $d_{diff}^{k2}$ may be normalized.

Similarly, the processing device 140 may optimize the at least one parameter using the gradient algorithm such that the objective function (e.g., Equation (7)) satisfies the optimization condition. Taking an objective function corresponding to one target region as an example (i.e., I or N is 1), the objective function corresponding to the target region may be determined according to Equation (13):

$$f_{obj}^1 = w_{11}(F_1 - C_{index1})^2 + w_{21}(S_1 - C_{index2})^2, \quad (13)$$

where $w_{11}$ represents a weight indicating the impact of the first conformity parameter of the target region on the value of the objective function $f_{obj}^1$, $w_{21}$ represents a weight indicating the impact of the second conformity parameter of the target region on the value of the objective function $f_{obj}^1$, $F_1$ represents the first conformity parameter corresponding to the target region, and $S_1$ represents the second conformity parameter corresponding to the target region.

For an $i^{th}$ grid region among the plurality of grid regions in the target region, a gradient with respect to the $i^{th}$ grid region may be determined according to Equation (14):

$$Grad_{k1} = \frac{2 \times w_{11} \times (F_1 - C_{index\,1}) \times f_{der-sigmoid}(d_{diff}^{k1}) \times V_{ptv-i}}{TV} - \frac{2 \times w_{21} \times (S_1 - C_{index\,2}) \times [f_{der-sigmoid}(d_{diff}^{k1}) \times V_{ptv-i} \times V_{RI} - V\_RI \times f_{der-sigmoid}(d_{diff}^{k1}) \times V_{i-ext}]}{V\_RI \times V\_RI}. \quad (14)$$

For an $i^{th}$ grid region among the plurality of grid regions in the dose region, a gradient with respect to the $i^{th}$ grid region may be determined according to Equation (15):

$$Grad_{k2} = \frac{-2 \times w_{21} \times (F_1 - C_{index\,1}) \times TV\_RI \times f_{der-sigmoid}(d_{diff}^{k2}) \times V_{ext-i})}{V\_RI \times V\_RI}. \quad (15)$$

In some embodiments, the processing device 140 may determine the at least one parameter using a machine learning model. For example, the processing device 140 may obtain a target image of the subject, generate a predicted image based on the target image and a dose region prediction model, and determine the at least one parameter based on the predicted image. More descriptions regarding the determination of the at least one parameter may be found elsewhere in the present disclosure (e.g., FIGS. 8-10 and the descriptions thereof).

In some embodiments, the processing device 140 may further update the at least one parameter. For example, the processing device 140 may obtain a target image of a subject, determine a plurality of sampling points in a vicinity of a boundary of the target region based on the target image, determine one or more dose control points by using at least one filter to filter the plurality of sampling points, and update the at least one parameter based on the one or more dose control points. More descriptions regarding the update of the at least one parameter may be found elsewhere in the present disclosure (e.g., FIGS. 11-18 and the descriptions thereof).

In some embodiments, the processing device 140 may receive a user instruction for confirming or modifying the at least one determined parameter of the treatment plan. For example, the processing device 140 may cause the at least one determined parameter of the treatment plan to be displayed on a user interface, and the user may review and/or provide a user instruction for confirming or modifying the at least one determined parameter of the treatment plan through the user interface. After the least one determined parameter of the treatment plan is verified, the user may input a user instruction (e.g., a confirmation instruction, a modification instruction, a re-generation instruction for performing the optimization again based on the at least one parameter retrieved from a preliminary treatment plan (before an optimization is performed) or obtained from the optimization already performed), and the processing device 140 may process the at least one determined parameter of the treatment plan based on the user instruction.

In 308, the processing device 140 (e.g., the control module 230) may cause the radiation system (e.g., the radiation system 100 illustrated in FIG. 1) to execute the treatment plan.

In some embodiments, the processing device 140 may position, based on the treatment plan, a radiation source to deliver at least one radiation beam to the target region. For example, a radiation source of the radiation system 100 (e.g., the radiation delivery device 110) may be directed to move to a target position, and deliver one or more radiation beams to a target region (e.g., a tumor) of a subject (e.g., a patient).

In some embodiments, the radiation system may include an MLC. The processing device 140 may cause a plurality of leaves of the MLC to move to collimate the at least one radiation beam such that the at least one radiation beam reaches the target region. For example, an MLC may include a plurality of leaves. The plurality of leaves of the MLC may form an aperture to allow a portion of the radiation beams to pass through according to a treatment plan. Accordingly, the portion of the radiation beams passing through the aperture may reach a target region of a subject to form a dose region and perform the radiation therapy.

According to some embodiments of the present disclosure, the treatment plan may be generated by optimizing the at least one parameter such that the objective function satisfies the optimization condition, which may improve the conformity between the target region and the dose region, thereby improving the efficiency and accuracy of the first shape of the dose region and/or the efficacy of the treatment plan.

Figure 6:
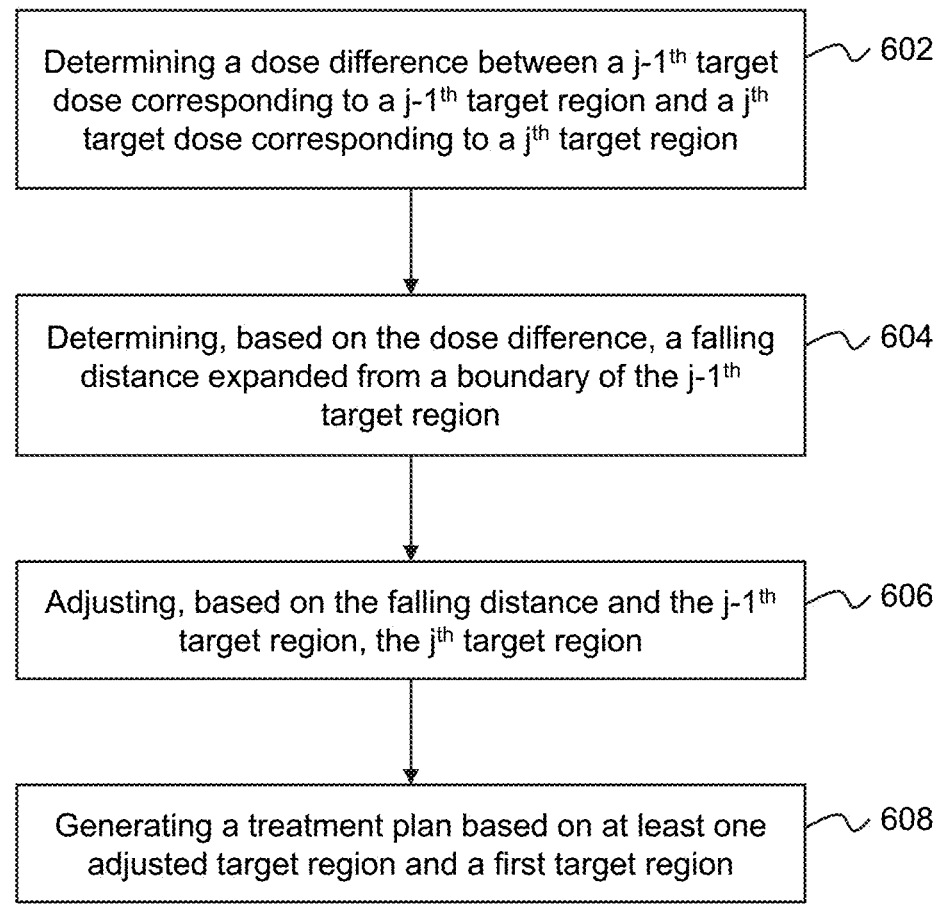
FIG. 6 is a flowchart illustrating an exemplary process for generating a treatment plan for irradiating a plurality of target regions at different target doses according to some embodiments of the present disclosure.

FIG. 6 is a flowchart illustrating an exemplary process 600 for generating a treatment plan for irradiating a plurality of target regions at different target doses according to some embodiments of the present disclosure. In some embodiments, the process 600 may be performed to achieve at least part of operation 304 as described in connection with FIG. 3.

In some embodiments, a plurality of target regions may be spatially separate, wherein the plurality of target regions are designated as a first target region, a second target region, . . . , an $m^{th}$ target region according to corresponding target doses from high to low. Since the plurality of target regions corresponds to different doses, a target region with a low target dose may have an effect on a target region with a high target dose, which may reduce the accuracy of a dose region determined based on the high target dose alone without considering the existence of a target region with a low target dose in a vicinity. In order to sequentially adjust at least one target region from the second target region to the $m^{th}$ target region, the process 600 may be performed. The first target region with the highest target dose may be determined based on methods described elsewhere in the present disclosure. See, e.g., FIG. ** and the description thereof.

In 602, for a $j^{th}$ target region among the second target region through the $m^{th}$ target region in which m is an integer greater than or equal to 2, and j is an integer within a range from 2 to m, the processing device 140 (e.g., the generation module 220) may determine a dose difference between a $j-1^{th}$ target dose corresponding to a $j-1^{th}$ target region and a $j^{th}$ target dose corresponding to a $j^{th}$ target region.

In some embodiments, the processing device 140 may obtain the target dose of one of the $2^{nd}$ through the $m^{th}$ target regions based on a treatment plan. For example, after a treatment plan is generated by a TPS associated with the radiation system 100, the processing device 140 may obtain the treatment plan from the TPS or a storage device that stores the treatment plan, and further obtain a target dose corresponding to each of multiple target regions from the treatment plan.

In some embodiments, the processing device 140 may determine the dose difference according to Equation (16):

$$D_{diff} = D_{j-1} - D_j, \quad (16)$$

where $D_{diff}$ represents the dose difference between the $j-1^{th}$ target dose corresponding to the $j-1^{th}$ target region and the $j^{th}$ target dose corresponding to the $j^{th}$ target region, $D_{j-1}$ represents the $j-1^{th}$ target dose corresponding to the $j-1^{th}$ target region, and $D_j$ represents the $j^{th}$ target dose corresponding to the $j^{th}$ target region.

In 604, the processing device 140 (e.g., the generation module 220) may determine, based on the dose difference, a falling distance expanded from a boundary of the $j-1^{th}$ target region.

The falling distance may refer to an expansion distance that is used to reduce or eliminate an interference of a target region with a low target dose with a target region with a high target dose.

In some embodiments, the processing device 140 may determine the falling distance expanded from the boundary of the $j-1^{th}$ target region based on the dose difference and a dose falling gradient (also referred to as a dose falloff). For example, the falling distance may be determined according to Equation (17):

$$L = \frac{D_{diff}}{t}, \quad (17)$$

where L represents the falling distance expanded from the boundary of the $j-1^{th}$ target region, and t represents the dose falling gradient.

In some embodiments, the dose falling gradient may be determined based on a system default setting or set manually by a user, such as, 100 cGy/mm, 200 cGy/mm, etc.

In 606, the processing device 140 (e.g., the generation module 220) may adjust, based on the falling distance and the $j-1^{th}$ target region, the $j^{th}$ target region.

In some embodiments, the processing device 140 may determine, based on the falling distance and a boundary of the $j-1^{th}$ target region, an extension region corresponding to the $j^{th}$ target region. For example, the processing device 140 may determine the extension region corresponding to the $j^{th}$ target region using an image extrapolation algorithm. For instance, the falling distance and the $j-1^{th}$ target region may be input into an image extrapolation model, and the image extrapolation model may output the extension region corresponding to the $j^{th}$ target region.

In some embodiments, the processing device 140 may determine an adjusted $j^{th}$ target region based on the $j^{th}$ target region and the extension region corresponding to the $j^{th}$ target region. For example, the processing device 140 may determine the adjusted $j^{th}$ target region by combining the $j^{th}$ target region and the extension region corresponding to the $j^{th}$ target region.

In 608, the processing device 140 (e.g., the generation module 220) may generate the treatment plan based on at least one adjusted target region and the first target region.

In some embodiments, for each target region of the first target region and the at least one adjusted target region, the processing device 140 may generate the treatment plan according to operations 302-306. For example, the processing device 140 may obtain at least one parameter of a dose region corresponding to the target region. The least one parameter may relate to the dose region where is enclosed by an isodose curve. The processing device 140 may obtain an objective function corresponding to the target region. The objective function may represent a conformity between the target region and the dose region. Further, the processing device 140 may optimize the at least one parameter such that the objective function satisfies an optimization condition, and generate the treatment plan based on a plurality of optimized parameters.

FIG. 7 is a schematic diagram illustrating an exemplary process for adjusting a target region according to some embodiments of the present disclosure.

As illustrated in FIG. 7, a subject (e.g., a patient including nasopharynx cancer) may include a first target region 702 and a second target region 704. A first target dose corresponding to the first target region 702 may be 6000 cGy, and a second target dose corresponding to the second target region 704 may be 5400 cGy. An optimization of a portion of a treatment plan corresponding to the first target region 702 may be performed according to operations 302-306, and an optimization of a portion of the treatment plan corresponding to the second target region 704 may be performed according to operations 602-608. Firstly, a falling distance may be determined according to Equations 16 and 17. For example, if a dose falling gradient is 200 cGy/mm, a falling distance between the first target region 702 and the second target region 704 may be 3 millimeters. And then, an extension region 706 corresponding to the second target region 704 may be determined based on the falling distance (i.e., 3 millimeters) and the first target region 702. Therefore, the adjusted second target region may include the extension region 706 and the second target region 704. Accordingly, the optimization of the portion of the treatment plan corresponding to the second target region 704 may be performed based on the adjusted second target region (i.e., the extension region 706 and the second target region 704).

According to some embodiments of the present disclosure, the target region with the low target dose (i.e., the low dose region) may be adjusted based on the dose difference, which may eliminate or reduce the interference of the target region with the low target dose with the target region with the high target dose, thereby improving the accuracy of the treatment plan so determined/optimized.

Figure 8:
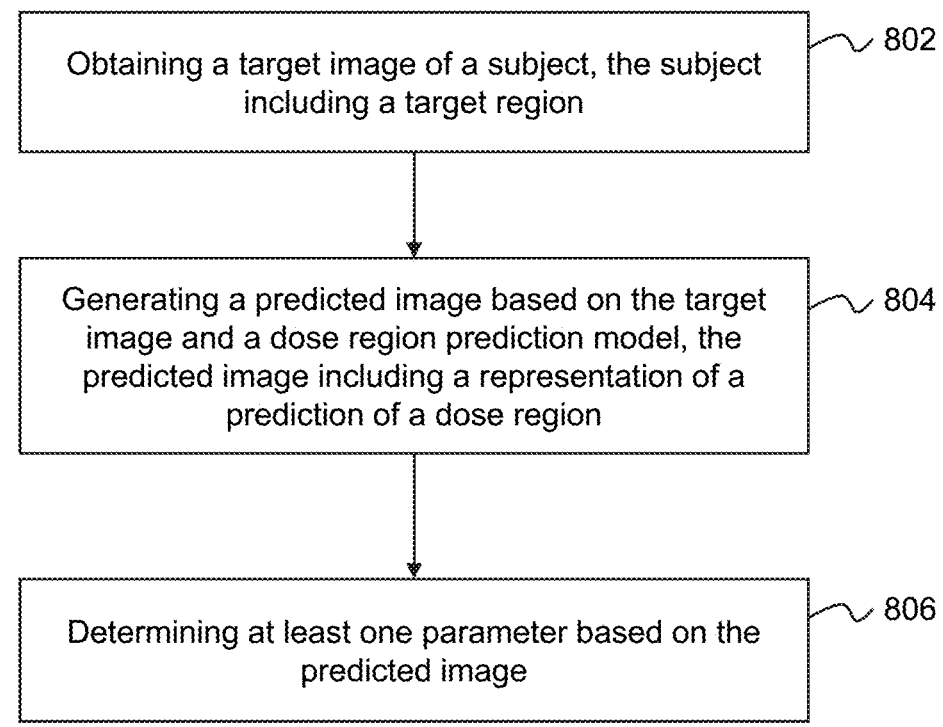
FIG. 8 is a flowchart illustrating an exemplary process for determining at least one parameter according to some embodiments of the present disclosure.

FIG. 8 is a flowchart illustrating an exemplary process 800 for determining at least one parameter according to some embodiments of the present disclosure. In some embodiments, the process 800 may be performed to achieve at least part of operation 306 as described in connection with FIG. 3.

In some embodiments, a target region may include a target to be irradiated at a target dose or a low dose region to be irradiated at a dose lower than the target dose. The low dose region may include a region in a vicinity of the target. According to a treatment plan, the low dose region may be subjected to a radiation dose below the target dose for the target, e.g., 80% of the target dose. The low dose region may lack a clear morphological character to facilitate its identification or delineation. Accordingly, different from the target, the low dose region may be difficult to be delineated by directly segmenting a target image. At present, a shape of the low dose region may be determined by performing an external expansion on the target. For example, a boundary of the target may be expanded by 1 centimeter, and the expansion region outside the boundary of the target may be determined as a low dose region. However, the target and the expansion region may need to be manually determined, which may be troublesome, and the low dose region so determined may be inaccurate and dependent on user experience. In addition, a conformity between a target region and a dose region may be poor. The process 800 may be performed to automatically determine the low dose region.

In 802, the processing device 140 (e.g., the obtaining module 210) may obtain a target image of a subject. The subject may include a target region.

The target image refers to an image of the subject that is used to determine the target region. The target region may include a target to be irradiated at a target dose and/or a low dose region to be irradiated at a dose lower than the target dose.

In some embodiments, the target image of the subject may include a medical image including morphological information of the subject. Exemplary target images may include a computed tomography (CT) image, a magnetic resonance (MR) image, a positron emission computed tomography (PET) image, an X-ray image, an ultrasound image, or the like. In some embodiments, the target image may be a 3-dimensional image including a plurality of slices.

In some embodiments, the processing device 140 may obtain the target image from a medical imaging device (e.g., a CT device, an MR device, a PET device, etc.) or a storage device (e.g., the storage device 150, a database, or an external storage device) that stores the target image of the subject.

In 804, the processing device 140 (e.g., the generation module 220) may generate a predicted image based on the target image and a dose region prediction model. The predicted image may include a representation of a prediction of a dose region.

The dose region prediction model may include a deep neural network that is configured to determine a first shape of the dose region based on the target image. For example, the dose region prediction model may be a 3D-UNet model.

In some embodiments, the dose region prediction model may be trained based on a plurality of training samples. A training sample may include a sample image and a sample reference image in which a sample dose region is labeled. More descriptions regarding the generation of the dose region prediction model may be found elsewhere in the present disclosure (e.g., FIGS. 9-10 and the descriptions thereof).

In some embodiments, the processing device 140 may input the target image into the dose region prediction model, and the dose region prediction model may output the predicted image including the representation of the prediction of the dose region.

In 806, the processing device 140 (e.g., the generation module 220) may determine at least one parameter based on the predicted image.

In some embodiments, the processing device 140 may obtain the first shape of the dose region based on the predicted image, and determine the at least one parameter by performing operations 302-306. For example, the processing device 140 may obtain at least one parameter from a treatment plan, obtain an objective function corresponding to the target region based on the predicted image, and optimize the at least one parameter such that the objective function satisfies an optimization condition. In some embodiments, the objective function may be the same as or similar to one or more of equations (3), (6), and (7) described elsewhere in the present disclosure.

In some embodiments, the processing device 140 may input the predicted image into a TPS, and the TPS may generate a preliminary treatment plan based on the predicted image. Further, the processing device 140 may determine the treatment plan based on the preliminary treatment plan by performing operations 302-306.

In some embodiments, the processing device 140 may receive a user instruction for confirming or modifying the at least one determined parameter of the treatment plan. More descriptions regarding the verification of the at least one determined parameter may be found elsewhere in the present disclosure (e.g., FIG. 3 and the descriptions thereof).

According to some embodiments of the present disclosure, the predicted image may be generated based on the target image and the dose region prediction model, and the at least one parameter may be determined based on the predicted image. Therefore, the target region and/or the dose region may be automatically determined, which may reduce a workload of the user, cross-user variations, and/or dependency on user experience, and improve the efficiency of the optimization process. In addition, the predicted image may be generated using the dose region prediction model, which may improve the accuracy of the image segmentation, thereby improving the accuracy of the optimization process.

Figures 9, 10:
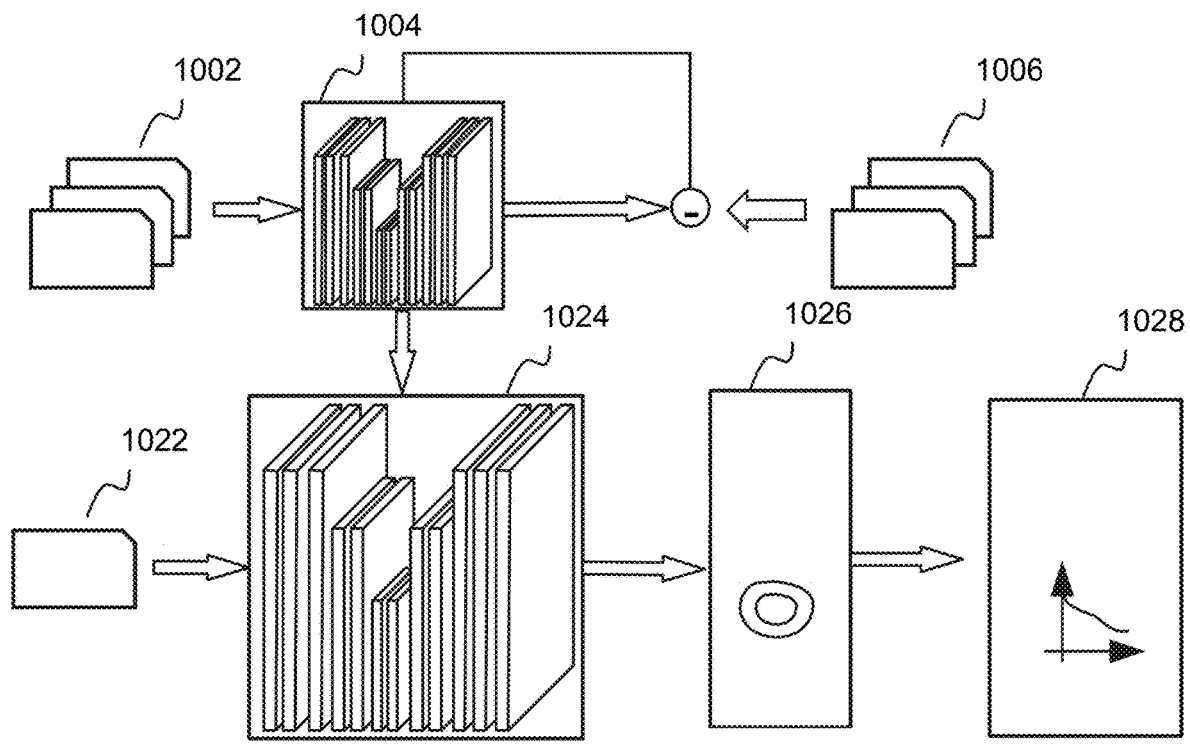
FIG. 9 is a flowchart illustrating an exemplary process for generating a dose region prediction model according to some embodiments of the present disclosure.
FIG. 10 is a schematic diagram illustrating an exemplary process for determining at least one parameter according to some embodiments of the present disclosure.

FIG. 9 is a flowchart illustrating an exemplary process 900 for generating a dose region prediction model according to some embodiments of the present disclosure. In some embodiments, the dose region prediction model described in connection with operation 804 in FIG. 8 may be obtained according to the process 900. In some embodiments, the process 900 may be performed by the radiation system 100. In some embodiments, the process 900 may be performed by another device or system other than the radiation system 100, e.g., a device or system of a vendor of a manufacturer.

In 902, the processing device 140 (e.g., the obtaining module 210) may obtain a plurality of training samples. A training sample may include a sample image and a sample reference image in which a sample dose region is labeled.

In some embodiments, each of at least some of the plurality of training samples may be obtained from historical treatment plans of one or more sample subjects. In some embodiments, the sample image of a training sample may be obtained by scanning a sample subject using a medical imaging device. For example, a sample image may be obtained similar to the obtaining of the target image described in operation 802. In some embodiments, a training sample may be obtained from a historical treatment plan determined or optimized according to the process 300 illustrated in FIG. 3. In some embodiments, the sample reference image of a training sample may include multiple dose regions; the historical treatment plan from which the sample image and the sample reference image of the training sample are obtained may have been determined/optimized according to the process 600 illustrated in FIG. 6.

In 904, the processing device 140 (e.g., the generation module 220) may generate a dose region prediction model by training an initial model using the plurality of training samples.

The training may include an iterative process. The plurality of training samples may be used to iteratively update model parameter(s) until a termination condition is satisfied. Exemplary termination conditions may include that a result of a loss function corresponding to the dose region prediction model is below a loss function value threshold, a variation between results of the loss function of a plurality of consecutive iterations of the iterative process for training the initial model is below a variation threshold, etc. More descriptions regarding the generation of the dose region prediction model may be found elsewhere in the present disclosure (e.g., FIG. 10 and the descriptions thereof).

For example, the processing device 140 may obtain 200 sets of medical data of sample subjects. Each set of medical data of a sample subject may include a sample image and a sample reference image in which one or more dose regions are labeled. A portion (e.g., 150 sets) of the 200 sets of medical data may be used as training sets to train the initial model, a portion (e.g., 25 sets) of the 200 sets of medical data may be used as verification sets, and a portion (e.g., 25 sets) of the 200 sets of medical data may be used as test sets. After the dose region prediction model is generated, the dose region prediction model may be used to generate a predicted image including a representation of a prediction of one or more dose regions based on a target image.

It should be understood that the plurality of sample images and the plurality of sample reference images may include a same type of target region. For example, the 200 sets of medical data may relate to rectal cancer, and the dose region prediction model may be used for predicting a dose region directed to treating the rectal cancer. As another example, the 200 sets of medical data may relate to breast cancer, and the dose region prediction model may be used for predicting a dose region directed to treating the breast cancer. As still another example, the 200 sets of medical data may relate to pancreatic cancer, and the dose region prediction model may be used for predicting a dose region directed to treating the pancreatic cancer.

FIG. 10 is a schematic diagram illustrating an exemplary process 1000 for determining at least one parameter according to some embodiments of the present disclosure.

As shown in FIG. 10, in some embodiments, a target image 1022 of a subject may be input into a dose region prediction model 1024, and the dose region prediction model 1024 may output a predicted image 1026. At least one parameter 1028 may be determined based on the predicted image 1026.

In some embodiments, the dose region prediction model 1024 may include a 3D-UNet model.

In some embodiments, the dose region prediction model 1024 may be obtained by training an initial model 1004 based on a plurality of training samples. A training sample may include a sample image 1002 and a sample reference image 1006 in which a sample dose region is labeled. In some embodiments, the sample image 1002 of a sample target region inside a sample subject may be determined as an input of the initial model 1004, and a sample reference image 1006 in which a sample dose region is labeled may be determined as a label.

In some embodiments, each of at least some of the plurality of training sample images may be obtained from historical treatment plans of one or more sample subjects. In some embodiments, the sample image of a training sample may be obtained by scanning a sample subject using a medical imaging device. For example, a sample image may be obtained similar to the obtaining of the target image described in operation 802. In some embodiments, a training sample may be obtained from a historical treatment determined or optimized according to the process 300 illustrated in FIG. 3. In some embodiments, the sample reference image of a training sample may include multiple dose regions; the historical treatment plan from which the sample image and the sample reference image of the training sample are obtained may have been determined/optimized according to the process 600 illustrated in FIG. 6. In some embodiments, the processing device 140 may obtain the plurality of training samples by retrieving (e.g., through a data interface) a database or a storage device.

During the training of the initial model 1004, the plurality of sample images 1002 and the plurality of sample reference images 1006 may be input to the initial model 1004, and parameter(s) of the initial model 1004 may be updated through one or more iterations. For example, the processing device 140 may input each of the plurality of sample images 1002 into the initial model 1004, and obtain a prediction result. The processing device 140 may determine a loss function based on the prediction result and the label (i.e., the corresponding sample reference image 1006). The loss function may be associated with a difference between the prediction result and the label. The processing device 140 may adjust the parameter(s) of the initial model 1004 based on the loss function to reduce the difference between the prediction result and the label, for example, by continuously adjusting the parameter(s) of the initial model 1004 to reduce or minimize the loss function.

In some embodiments, the loss function may be a perceptual loss function, a squared loss function, a logistic regression loss function, etc.

In some embodiments, the dose region prediction model 1024 may also be obtained according to other training manners. For example, the dose region prediction model 1024 may be obtained based on an initial learning rate (e.g., 0.1) and/or an attenuation strategy using the plurality of sample images 1002 and the plurality of sample reference images 1006.

Figure 11:
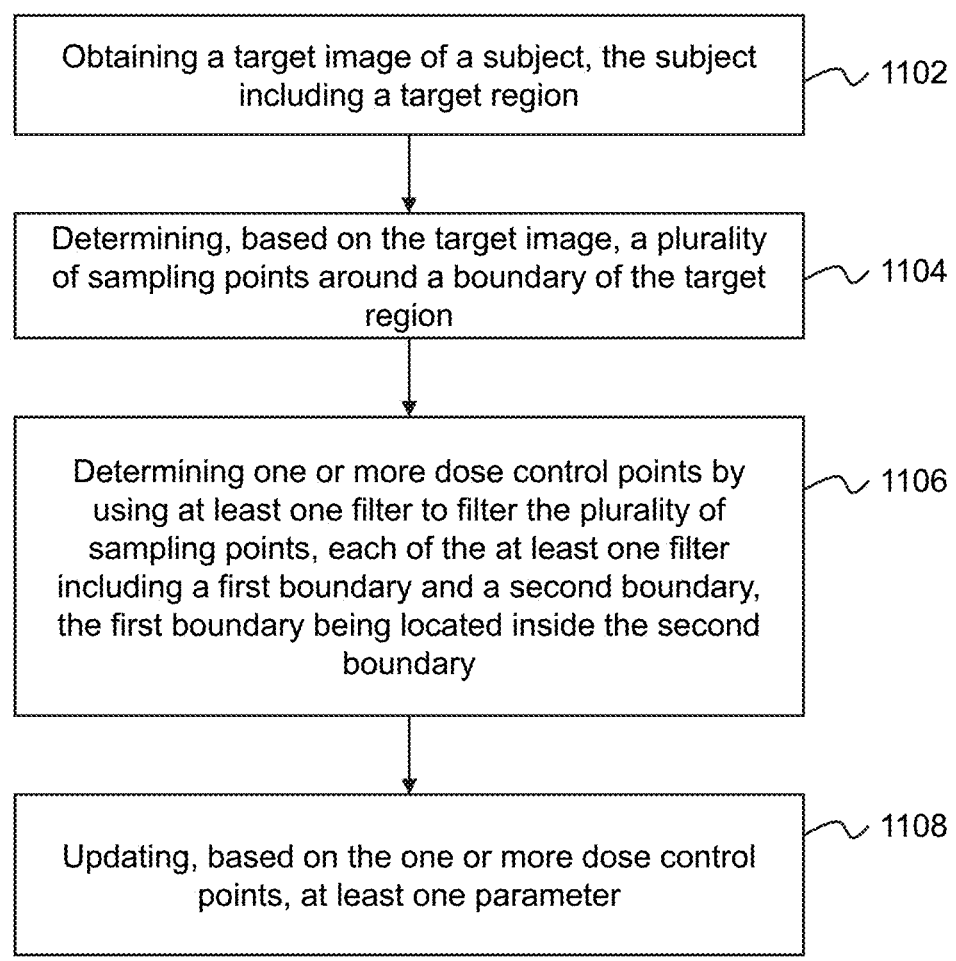
FIG. 11 is a flowchart illustrating an exemplary process for updating at least one parameter based on one or more dose control points according to some embodiments of the present disclosure.

FIG. 11 is a flowchart illustrating an exemplary process 1100 for updating at least one parameter based on one or more dose control points according to some embodiments of the present disclosure. In some embodiments, the process 1100 may be performed to achieve at least part of operation 306 as described in connection with FIG. 3.

In radiation therapy, a preliminary treatment plan may be optimized by improving a conformity between a dose region and a target region. At present, the conformity may be improved by manually adding an auxiliary region to an image of a subject, and controlling a dose of the auxiliary region. Alternatively, the conformity may be improved by manually adding an auxiliary region to the target region and optimizing a dose in a vicinity of the target region based on a dose falling gradient. However, the auxiliary region may be manually added, which is troublesome, and the position of the auxiliary region may be inaccurate and depend on user experience, thereby adversely affecting the conformity. In order to automatically improve the conformity, the process 1100 may be performed.

In 1102, the processing device 140 (e.g., the obtaining module 210) may obtain a target image of a subject. The subject may include a target region.

In some embodiments, the obtaining of the target image may be similar to the obtaining of the target image described in operation 802.

In some embodiments, the processing device 140 may pre-process the target image. For example, the processing device 140 may extract the target region from the target image based on an image segmentation algorithm, a machine learning model, etc.

In 1104, the processing device 140 (e.g., the generation module 220) may determine, based on the target image, a plurality of sampling points in a vicinity of a boundary of the target region.

A sampling point refers to a point where a dose is monitored for dose control. In some embodiments, the target image may be divided into a plurality of grid points, each of the plurality of grid points may be determined as a sampling point. For example, the processing device 140 may convert at least a portion of the target image into a plurality of grid points, and determine each of at least some of the plurality of grid points as a sampling point.

A vicinity of the target region may refer to a region around the boundary of the target region. In some embodiments, for each point in the vicinity, a minimum distance between the point of the vicinity and the boundary of the target region may be within a preset distance range. The preset distance range may be determined based on a system default setting or set manually by a user, such as, a range from 0 to 100 millimeters, a range from 0 to 200 millimeters, a range from 0 to 300 millimeters, a range from 0 to 500 millimeters, a range from 0 to 800 millimeters, a range from 0 to 1 centimeter, etc.

In some embodiments, the processing device 140 may determine one or more points in the vicinity of the boundary of the target region as the plurality of sampling points. For example, after at least a portion of a target image is converted into a plurality of grid points, the processing device 140 may determine, based on a preset distance range, a vicinity of a boundary of a target region represented in the target image, and determine one or more points in the vicinity of the boundary of the target region as a plurality of sampling points.

Figure 12:
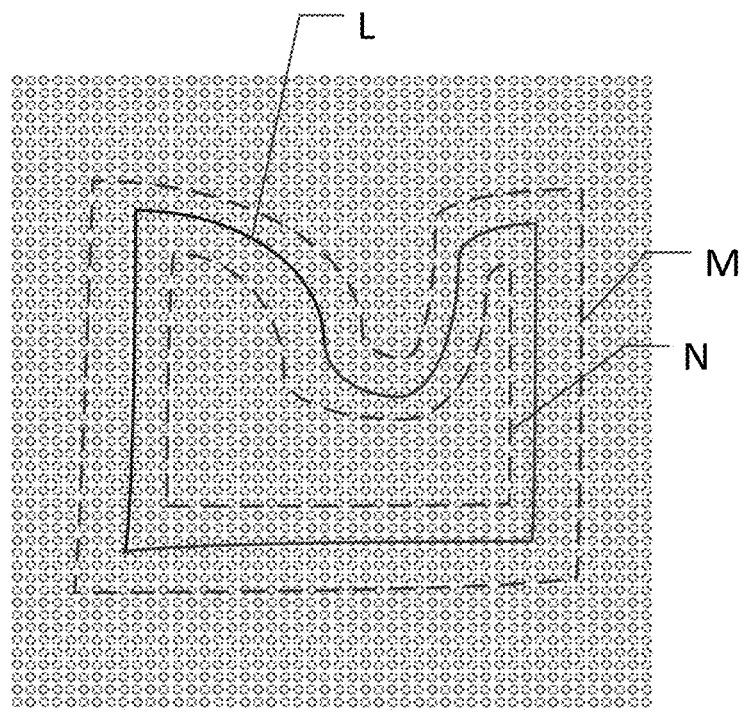
FIG. 12 is a schematic diagram illustrating an exemplary target image according to some embodiments of the present disclosure.

Merely by way of example, as illustrated in FIG. 12, a solid line "L" may be a boundary of a target region, and dotted lines "M" and "N" may be used to define a vicinity of the boundary of the target region. A plurality of grid points located in a region bounded by the dotted lines "M" and "N" may be determined as a plurality of sampling points.

By determining the plurality of sampling points in the vicinity of the boundary of the target region, a count of the plurality of sampling points may be reduced, which may reduce a workload of subsequent operation(s).

In some embodiments, the processing device 140 may receive a user instruction for determining the plurality of sampling points based on the target image. For example, the processing device 140 may cause a target image to be displayed on a user interface, and the user may input a user instruction for determining a plurality of sampling points on the target image through the user interface. After the user instruction is received, the processing device 140 may determine the plurality of sampling points based on the user instruction.

In 1106, the processing device 140 (e.g., the generation module 220) may determine one or more dose control points by using at least one filter to filter the plurality of sampling points.

Figure 13:
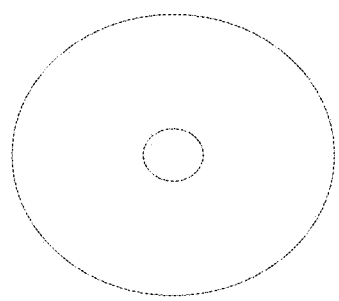
FIG. 13 is a schematic diagram illustrating an exemplary filter according to some embodiments of the present disclosure.

Each of the at least one filter may include a first boundary and a second boundary, wherein the first boundary is located inside the second boundary. The first boundary of each of the at least one filter may be a closed boundary (e.g., a closed circular boundary). The second boundary may be a closed boundary (e.g., a closed circular boundary). In some embodiments, the filter may be a two-dimensional (2D) filter or a three-dimensional (3D) filter. For example, the filter may be concentric circles or concentric spheres. Merely by way of example, as illustrated in FIG. 13, a filter may be two concentric circles.

A dose control point refers to a sampling point where a dose is monitored for dose control. In some embodiments, the plurality of sampling points may be filtered by using the at least one filter to determine the one or more dose control points. For example, for each of the plurality of sampling points, the processing device 140 may determine a parameter value of at least one contour parameter of the target region between the first boundary and the second boundary corresponding to the sampling point, and determine whether the sampling point is a dose control point based on the parameter value of the at least one contour parameter. More descriptions regarding the determination of the one or more dose control points may be found elsewhere in the present disclosure (e.g., FIG. 14 and the descriptions thereof).

In some embodiments, the plurality of sampling points may be filtered according to a certain rule. For example, the at least one filter may traverse the plurality of sampling points row by row (or column by column).

Figure 15:
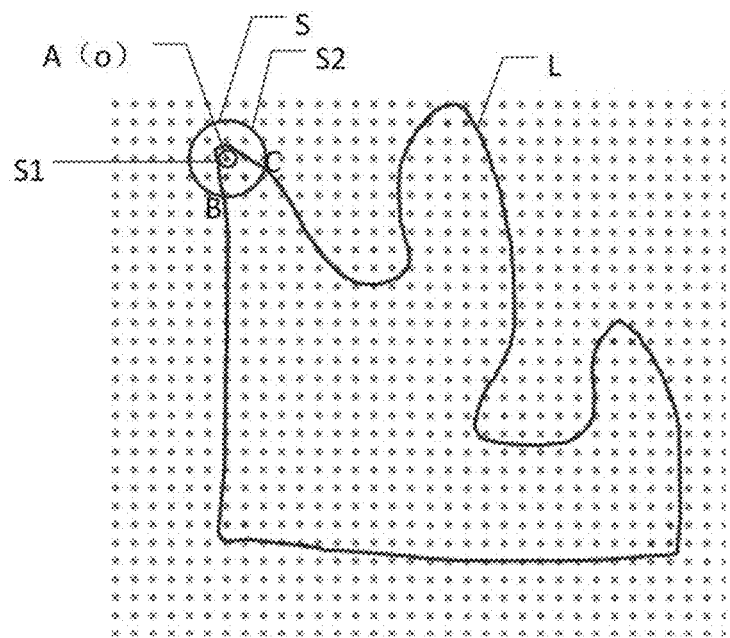
FIG. 15 is a schematic diagram illustrating an exemplary process for filtering a sampling point according to some embodiments of the present disclosure.

In some embodiments, since the first boundary is inside the second boundary, the first boundary may be used to determine a sampling point that is being filtered. For example, as illustrated in FIG. 15, a first boundary "S1" of a filter "S" may include a sampling point "A," and the sampling point "A" may be deemed the sampling point that is being filtered by the filter "S." At this time, the first boundary of the filter may not intersect the boundary of the target region, and the second boundary of the filter may intersect the boundary of the target region. Referring to FIG. 15, the first boundary "S1" of the filter "S" does not intersect the boundary "L" of the target region, and the second boundary "S2" of the filter "S" intersects the boundary "L" of the target region.

Figure 16:
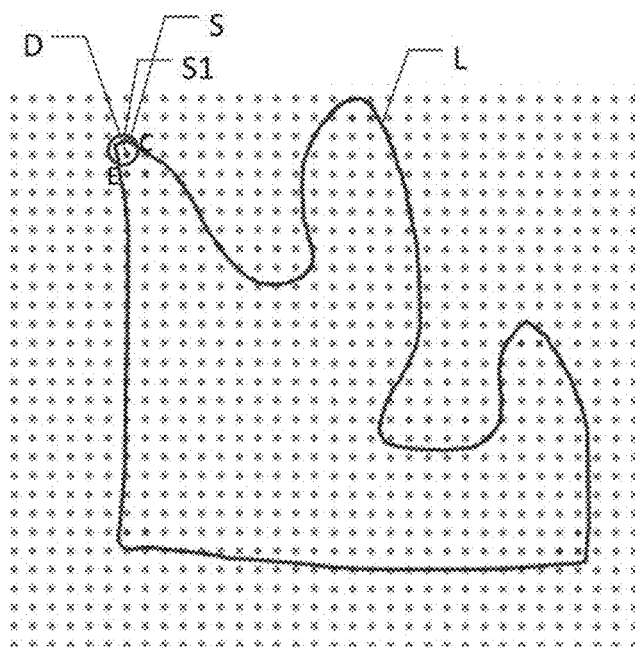
FIG. 16 is a schematic diagram illustrating an exemplary process for filtering a sampling point according to some embodiments of the present disclosure.

In some embodiments, a center of the filter may also be used to determine the sampling point that is being filtered. For example, as illustrated in FIG. 15, the filter may include one closed boundary; when a center "O" of the filter "S" is moved to a position of the sampling point "A," the sampling point "A" may be deemed as the sampling point that is being filtered. For example, as illustrated in FIG. 16, a filter "S" including a closed boundary "S1" may be used to filter a plurality of sampling points. In some embodiments, the filter may be a 2D filter or a 3D filter. For example, the filter may be a circle or a sphere.

In some embodiments, the at least one filter may include a plurality of filters. The plurality of filters may traverse different portions of the target image to filter sampling points in these different portions, respectively. The plurality of filters may be used to filter the plurality of sampling points simultaneously or successively.

Merely by way of example, the at least one filter may include a first filter and a second filter, wherein the first filter may be used to filter one or more sampling points in a vicinity inside the boundary of the target region, and the second filter may be used to filter one or more sampling points in a vicinity outside the boundary of the target region. A size of the first filter may be the same as or different from a size of the second filter. In some embodiments, the first filter may include a first boundary, and the second filter may include a second boundary. For example, the first filter and the second filter may be concentric circles of a same size. As another example, the first filter and the second filter may be concentric circles of different sizes. As still another example, the first filter may be defined by concentric circles, and the second filter may be defined by concentric squares. Alternatively, the first filter may be defined by concentric spheres, and the second filter may be defined by concentric circles. In some embodiments, the first filter and the second filter may each include one closed boundary. For example, the first filter and the second filter may be circles of a same size. As another example, the first filter and the second filter may be circles of different sizes. As still another example, the first filter may be a circle, and the second filter may be a sphere.

Figure 17:
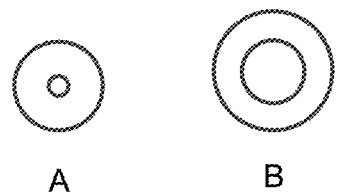
FIG. 17 is a schematic diagram illustrating exemplary filters according to some embodiments of the present disclosure.
Figure 18:
FIG. 18 is a schematic diagram illustrating exemplary filters according to some embodiments of the present disclosure.

In some embodiments, the processing device 140 may use the first filter to filter the one or more sampling points in the vicinity inside the boundary of the target region and use the second filter to filter the one or more sampling points in the vicinity outside the boundary of the target region simultaneously or successively. For example, as illustrated in FIG. 17, a first filter "A" and a second filter "B" may each be defined by concentric circles of different sizes. For instance, an outer radius of the first filter "A" may be less than an outer radius of the second filter "B." The first filter "A" may be used to filter the one or more sampling points in the vicinity inside the boundary of the target region, and the second filter "B" may be used to filter the one or more sampling points in the vicinity outside the boundary of the target region simultaneously or successively. Referring to FIGS. 12 and 17, the first filter "A" may be used to filter one or more sampling points in a region between the solid line "L" and the dotted line "N," and the second filter "B" may be used to filter one or more sampling points in a region between the solid line "L" and the dotted line "M." As another example, as illustrated in FIG. 18, a first filter "a" may include one circle, and a second filter "b" may include one circle, wherein a radius of the first filter "a" may be less than a radius of the second filter "b." The first filter "a" may be used to filter the one or more sampling points in the vicinity inside the boundary of the target region, and the second filter "b" may be used to filter the one or more sampling points in the vicinity outside the boundary of the target region simultaneously or successively. Referring to FIGS. 12 and 18, the first filter "a" may be used to filter one or more sampling points in a region between the solid line "L" and the dotted line "N," and the second filter "b" may be used to filter one or more sampling points in a region between the solid line "L" and the dotted line "M."

In some embodiments, when the plurality of filters are used to filter the plurality of sampling points simultaneously, a plurality of graphics processing units (GPUs) may be used to cause the plurality of filters to filter the plurality of sampling points. For example, the plurality of GPUs may be arranged in a parallel configuration, and the plurality of GPUs may be configured to determine the one or more dose control points by using the plurality of filters to filter the plurality of sampling points. In some embodiments, a count of the plurality of GPUs may be the same as a count of the plurality of filters. That is, each of the plurality of GPUs may correspond to one filter among the plurality of filters. In some embodiments, the count of the plurality of GPUs may be different from the count of the plurality of filters. That is, each of the plurality of GPUs may correspond to one or more filters among the plurality of filters.

By using the plurality of GPUs to cause the plurality of filters to filter the plurality of sampling points, the efficiency of the filtering operation may be improved, which may improve the efficiency of the determination of the one or more dose control points.

In 1108, the processing device 140 (e.g., the generation module 220) may update, based on the one or more dose control points, the at least one parameter.

In some embodiments, for each of the one or more dose control points, the processing device 140 may update the at least one parameter according to operations 302-306. For example, the processing device 140 may update, based on the one or more dose control points, the at least one parameter generated according to operations 302-306. As another example, after the one or more dose control points are determined, the processing device 140 may optimize the dose region based on the one or more dose control points, and generate the at least one parameter according to operations 302-306.

In some embodiments, the processing device 140 may determine a dose target corresponding to each of the one or more dose control points. The dose target may include a certain dose or a dose range. In some embodiments, different dose control points may correspond to different dose targets. Alternatively, different dose control points may correspond to a same dose target. For example, when a dose control point is determined, the processing device 140 may determine a dose target corresponding to the dose control point based on a position of the target region or a position of the dose control point relative to the target region, so as to optimize the at least one parameter.

In some embodiments, for each of the one or more dose control points, the processing device 140 may optimize a dose of the dose control point based on the dose target such that an objective function satisfies an optimization condition. Merely by way of example, the processing device 140 may optimize the preliminary treatment plan, based on a dose target, a dose of a dose control point using a dose optimization technique (e.g., a dose optimization model). For example, if the dose control point is a sampling point inside the target region, the dose target corresponding to the dose control point may be to adjust (e.g., increase) the dose of the dose control point to reach a first dose threshold, and the processing device 140 may optimize the preliminary treatment plan by adjusting (e.g., increasing) the dose of the dose control point to reach the first dose threshold using the dose optimization technique. Alternatively, if the dose control point is a sampling point outside the target region, the dose target corresponding to the dose control point may be to adjust (e.g., decrease) the dose of the dose control point to reach a second dose threshold, and the processing device 140 may optimize the preliminary treatment plan by adjusting (e.g., decreasing) the dose of the dose control point to reach the second dose threshold using the dose optimization technique. The first dose threshold and/or the second dose threshold may be determined based on a system default setting or set manually by a user. As another example, the processing device 140 may add first constraint(s) to the dose control point(s) inside the target region to further adjust (e.g., causing an increase in) the dose(s) of the dose control point(s) inside the target region, and add second constraint (s) to dose control point(s) outside the target region to further adjust (e.g., causing a decrease in) the dose(s) of the dose control point(s) outside the target region.

In some embodiments, the processing device 140 may further optimize dose(s) of sampling point(s) other than the one or more dose control points such that an objective function satisfies an optimization condition. In some embodiments, each of the sampling point(s) other than the one or more dose control points may correspond to a dose target. In some embodiments, a dose target corresponding to a sampling point other than the one or more dose control points may be different from a dose target corresponding to one of the one or more dose control points.

According to some embodiments of the present disclosure, the one or more dose control points may be determined by using the at least one filter to filter the plurality of sampling points, and the at least one parameter of the treatment plan may be updated based on the one or more dose control points, which may improve the efficiency and accuracy the optimization of dose(s) of the one or more dose control points, thereby improving the conformity between the target region and a dose region.

Figure 14:
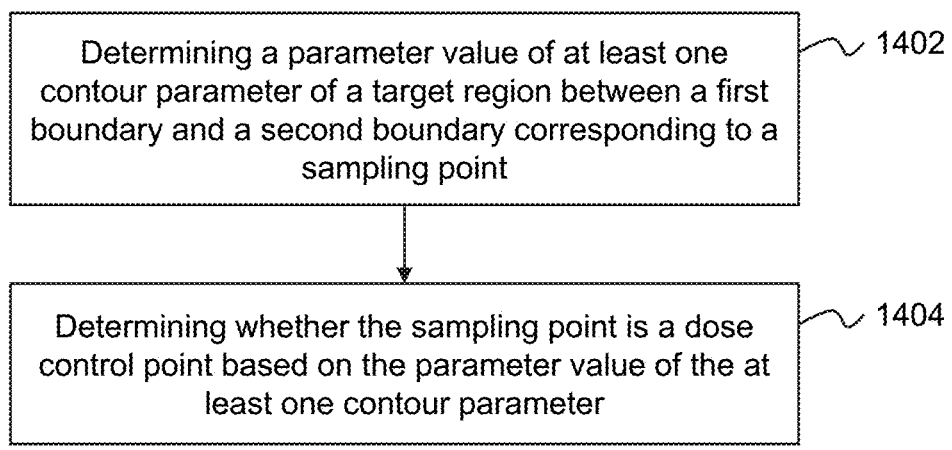
FIG. 14 is a flowchart illustrating an exemplary process for determining one or more dose control points according to some embodiments of the present disclosure.

It should be noted that the description of the process 1100 is provided for the purposes of illustration, and is not intended to limit the scope of the present disclosure. For persons having ordinary skills in the art, various variations and modifications may be conducted under the teaching of the present disclosure. However, those variations and modifications may not depart from the protection of the present disclosure.

FIG. 14 is a flowchart illustrating an exemplary process 1400 for determining one or more dose control points according to some embodiments of the present disclosure. In some embodiments, the process 1400 may be performed to achieve at least part of operation 1106 as described in connection with FIG. 11.

In 1402, the processing device 140 (e.g., the generation module 220) may determine a parameter value of at least one contour parameter of a target region between a first boundary and a second boundary of a filter corresponding to a sampling point.

The at least one contour parameter may include a length of a boundary corresponding to a portion of the target region between the first boundary and the second boundary of the filter, an area of a section of the target region that is bounded by the boundary corresponding to the portion of the target region and the first boundary and/or the second boundary of the filter, a count of grid point(s) on the boundary corresponding to the portion of the target region, a curvature of the boundary corresponding to the portion of the target region, etc.

In some embodiments, when a filter is used to filter a sampling point, the processing device 140 may determine whether a space or a region between the first boundary and the second boundary of the filter includes a boundary corresponding to a portion of the target region between the first boundary and the second boundary of the filter. If the space or the region between the first boundary and the second boundary includes the boundary corresponding to the portion of the target region between the first boundary and the second boundary of the filter, the processing device 140 may further determine the parameter value of the at least one contour parameter of the target region between the first boundary and the second boundary corresponding to the sampling point. For example, the processing device 140 may determine the length of the boundary corresponding to the portion of the target region between the first boundary and the second boundary and/or the area of the section of the target region that is bounded by the boundary corresponding to the portion of the target region and the first boundary and/or the second boundary of the filter. The area may be determined by establishing a coordinate system according to the target image. Therefore, each point on the target image may be represented by a coordinate in the coordinate system, and the length of the boundary corresponding to the portion of the target region between the first boundary and the second boundary of the filter and/or the area of the section of the target region that is bounded by the boundary corresponding to the portion of the target region and the first boundary and/or the second boundary may be determined based on coordinates of points in the portion on the target image. As another example, the processing device 140 may determine the count of grid point(s) on the boundary corresponding to the portion of the target region based on an image recognition algorithm.

If the space or the region between the first boundary and the second boundary includes no boundary corresponding to the target region, the processing device 140 may determine that the sampling point is too far away from the boundary of the target region and not a dose control point. Accordingly, the dose of the sampling point may be optimized by performing operations 302-306.

In 1404, the processing device 140 (e.g., the generation module 220) may determine whether the sampling point is a dose control point based on the parameter value of the at least one contour parameter.

In some embodiments, the processing device 140 may determine whether the parameter value of the at least one contour parameter satisfies a preset condition. The preset condition may include that the length of the boundary corresponding to the portion of the target region between the first boundary and the second boundary exceeds a length threshold, the area of the region bounded by the boundary corresponding to the portion of the target region and the first boundary or the second boundary exceeds an area threshold, the count of grid point(s) on the boundary corresponding to the portion of the target region exceeds a count threshold, the curvature of the boundary corresponding to the portion of the target region exceeds a curvature threshold, etc. In some embodiments, each of the length threshold, the area threshold, the count threshold, and the curvature threshold may be determined based on a system default setting or set manually by a user.

If the parameter value of the at least one contour parameter satisfies the preset condition (e.g., the length of the boundary exceeding the length threshold, the area of the region exceeding the area threshold, the count of grid point(s) on the boundary exceeding the count threshold, the curvature of the boundary corresponding to the portion of the target region exceeding the curvature threshold), the curvature of the boundary may be large, and the sampling point being filtered by the filter may be deemed located on a concave or convex of the target region. Therefore, the processing device 140 may determine the sampling point as the dose control point.

If the parameter value of the at least one contour parameter doesn't satisfy the preset condition (e.g., the length of the boundary being below the length threshold, the area of the region being below the area threshold, the count of grid point(s) on the boundary being below the count threshold, the curvature of the boundary corresponding to the portion of the target region being below the curvature threshold), the curvature of the boundary may be small, and the sampling point being filtered by the filter may be deemed located at or near a flat portion of the boundary of the target region, in which the flat portion of the boundary has a low curvature. Therefore, the processing device 140 may determine the sampling point not a dose control point.

FIG. 15 is a schematic diagram illustrating an exemplary process for filtering a sampling point according to some embodiments of the present disclosure. As illustrated in FIG. 15, a filter "S" may be used to filter a plurality of sampling points in a target region. The filter "S" may include a first boundary "S1" and a second boundary "S2." A boundary of the target region may be represented by "L." The filter "S" may be moved to a sampling point "A" to filter the sampling point "A." For instance, a center "O" of the filter "S" may be moved to a position of the sampling point "A." When the filter "S" is located at the sampling point "A," a boundary of the target region between the first boundary "S1" and the second boundary "S2" may be a curve between points "B" and "C" (also referred to as a curve "BC"). A parameter value of at least one contour parameter of the boundary (i.e., the curve "BC") may be determined, and whether the sampling point "A" is a dose control point may be determined based on the parameter value of the at least one contour parameter of the curve "BC." For example, whether the sampling point "A" is the dose control point may be determined based on a length of the curve "BC." As another example, whether the sampling point "A" is the dose control point may be determined based on an area of a region bounded by the curve "BC" and the filter "S." As still another example, whether the sampling point "A" is the dose control point may be determined based on a count of grid point(s) on the curve "BC."

In some embodiments, since the first boundary is inside the second boundary, the first boundary may be used to determine a sampling point that is being filtered. For example, as illustrated in FIG. 15, the center "O" of the filter "S" may be moved to the position of the sampling point "A." That is, the first boundary "S1" of the filter "S" may include the sampling point "A," and the sampling point "A" may be considered the sampling point that is being filtered. At this time, the first boundary of the filter does not intersect the boundary of the target region, and the second boundary of the filter intersects the boundary of the target region. Referring to FIG. 15, the first boundary "S1" of the filter "S" does not intersect the boundary "L" of the target region, and the second boundary "S2" of the filter "S" intersects the boundary "L" of the target region.

FIG. 16 is a schematic diagram illustrating an exemplary process for filtering a sampling point according to some embodiments of the present disclosure. As illustrated in FIG. 16, a filter "S" may be used to filter a plurality of sampling points in a target region. The filter "S" may include a closed boundary "S1." A boundary of the target region may be represented by "L." The filter "S" may be moved to a sampling point "D" to filter the sampling point "D." For instance, a center of the filter "S" may be moved to a position of the sampling point "D." When the filter "S" is located at the sampling point "D," a boundary of the target region bounded by the closed boundary "S1" may be a curve between points "C" and "E" (also referred to as a curve "CE"). A parameter value of at least one contour parameter of the boundary (i.e., the curve "CE") may be determined, and whether the sampling point "D" is a dose control point may be determined based on the parameter value of the at least one contour parameter of the curve "CE." For example, whether the sampling point "D" is the dose control point may be determined based on a length of the curve "CE." As another example, whether the sampling point "D" is the dose control point may be determined based on an area of a region bounded by the curve "CE" and the filter "S." As still another example, whether the sampling point "D" is the dose control point may be determined a count of grid point(s) on the curve "CE."

In some embodiments, a preset threshold (e.g., the length threshold, the area threshold, the count threshold, the curvature threshold) may be altered. For example, the preset threshold may be altered based on intersection points between the boundary of the target region and the filter. For example, as illustrated in FIG. 16, the preset threshold may be determined based on a chord formed according to the curve "CE," a chord where a point on the curve "CE" closest to the center of the filter is located, a chord with a shortest distance from a center of the filter to a point on the curve "CE," etc. It is understood that these examples are provided for illustration purposes and not intended to be limiting. In some embodiments, the preset threshold may be a multiple of the chord, such as 1.0, 1.1, 1.2, 1.3, etc.

According to some embodiments, whether the sampling point is the dose control point may be determined based on the parameter value of the at least one contour parameter. In some embodiments, the one or more dose control points may be identified by filtering sampling point(s) located on the concave or convex of the target region from the plurality of sampling points. Therefore, dose(s) of the one or more dose control points may be optimized to improve the conformity between the target region and a dose region.

It should be noted that the descriptions of the processes 300, 600, 800, 900, 1100, and 1400 are provided for the purposes of illustration, and are not intended to limit the scope of the present disclosure. For persons having ordinary skills in the art, various variations and modifications may be conducted under the teaching of the present disclosure. However, those variations and modifications may not depart from the protection of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in a combination of one or more programming languages, including an subject-oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, for example, an installation on an existing server or mobile device.

Similarly, it should be appreciated that in the foregoing description of embodiments of the present disclosure, various features are sometimes grouped in a single embodiment, figure, or descriptions thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for generating a treatment plan for irradiating, using a radiation system, a target region, implemented on a computing device having at least one processor and at least one storage device, the method comprising:
    obtaining at least one parameter from the treatment plan, the at least one parameter relating to a dose region, wherein the dose region is enclosed by an isodose curve;
    obtaining an objective function corresponding to the target region, the objective function representing a conformity between the target region and the dose region, wherein the objective function includes at least one conformity parameter relating to a first volume of an intersection region between the target region and the dose region; and
    generating the treatment plan by optimizing the at least one parameter such that the objective function satisfies an optimization condition, wherein the first volume of the intersection region is determined by:
        dividing the target region into a plurality of grid regions;
        determining a dose of each of the plurality of grid regions of the target region;
        identifying one or more grid regions from the plurality of grid regions of the target region, wherein for each of the one or more grid regions of the target region, a radiation dose of the grid region satisfies a first dose condition; and
        determining the first volume of the intersection region based on the one or more grid regions.

2. The method of claim 1, the objective function including at least one of a first conformity parameter or a second conformity parameter, wherein
    the first conformity parameter represents a first ratio of the first volume of the intersection region to a second volume of the dose region, and
    the second conformity parameter represents a second ratio of the first volume of the intersection region to a third volume of the target region.

3. The method of claim 2, further including determining the second volume of the dose region by:
    dividing a surface of the subject into a plurality of grid regions;

determining a dose of each of the plurality of grid regions of the surface;
identifying one or more grid regions from the plurality of grid regions of surface, wherein for each of the one or more grid regions, a radiation dose of the grid region satisfies a second dose condition; and
determining the second volume of the dose region based on the one or more grid regions.

4. The method of claim 2, wherein the objective function further corresponds to a target dose, and the target region includes at least one of a target to be irradiated at the target dose or a low dose region to be irradiated at a dose lower than the target dose.

5. The method of claim 4, wherein the low dose region includes a region that abuts the target, and the low dose region is determined by:
obtaining a dose difference between the target dose and the dose of the low dose region;
determining, based on the dose difference, a falling distance expanded from a boundary of the target; and
adjusting, based on the falling distance, the low dose region.

6. The method of claim 1, wherein the optimization condition includes at least one of:
a result of the objective function is below an objective function value threshold, or
a variation between results of the objective function of a plurality of consecutive iterations of an iterative process for generating the treatment plan is below a variation threshold.

7. The method of claim 1, wherein the optimizing the at least one parameter such that the objective function satisfies an optimization condition includes:
obtaining a target image of a subject, the subject including the target region;
generating a predicted image based on the target image and a dose region prediction model, the predicted image including a representation of a prediction of the dose region; and
optimizing the at least one parameter based on the predicted image such that the objective function satisfies an optimization condition.

8. The method of claim 7, wherein the dose region prediction model is generated according to a process including:
obtaining a plurality of training samples, a training sample including a sample image and a sample reference image in which a sample dose region is labeled; and
generating the dose region prediction model by training an initial model using the plurality of training samples.

9. The method of claim 1, further comprising:
obtaining a target image of a subject, the subject including the target region;
determining, based on the target image, a plurality of sampling points in a vicinity of a boundary of the target region;
determining one or more dose control points by using at least one filter to filter the plurality of sampling points, each of the at least one filter including a first boundary and a second boundary, the first boundary being located inside the second boundary; and
updating, based on the one or more dose control points, the at least one parameter.

10. The method of claim 9, wherein the determining one or more dose control points by using at least one filter to filter the plurality of sampling points includes: for each of the plurality of sampling points,
determining a parameter value of at least one contour parameter of the target region between the first boundary and the second boundary corresponding to the sampling point; and
determining whether the sampling point is a dose control point based on the parameter value of the at least one contour parameter.

11. The method of claim 9, wherein
the method is implemented by a plurality of graphics processing units (GPUs) in a parallel configuration,
the at least one filter includes a plurality of filters, and
the plurality of GPUs are configured to determine the one or more dose control points by using the plurality of filters to filter the plurality of sampling points.

12. The method of claim 1, further comprising:
verifying the at least one determined parameter of the treatment plan based on a user instruction.

13. The method of claim 1, further comprising:
causing the radiation system to execute the treatment plan.

14. The method of claim 13, wherein the causing the radiation system to execute the treatment plan comprises:
positioning, based on the treatment plan, a radiation source to deliver at least one radiation beam to the target region.

15. The method of claim 1, wherein the target region includes a plurality of target regions at different target doses, the plurality of target regions being spatially separate, wherein the plurality of target regions are designated as a first target region, a second target region, . . . , an $m^{th}$ target region according to corresponding target doses from high to low, the method further comprising:
sequentially adjusting at least one target region from the second target region to the $m^{th}$ target region, wherein
for a $j^{th}$ target region among the second target region through the $m^{th}$ target region in which m is an integer greater than or equal to 2, and j is an integer within a range from 2 to m,
determining a dose difference between a $j-1^{th}$ target dose corresponding to a $j-1^{th}$ target region and a $j^{th}$ target dose corresponding to a $j^{th}$ target region;
determining, based on the dose difference, a falling distance expanded from a $j-1^{th}$ boundary of the $j-1^{th}$ target region; and
adjusting, based on the falling distance and the $j-1^{th}$ target region, the $j^{th}$ target region; and
generating the treatment plan based on at least one adjusted target region and the first target region.

16. The method of claim 15, wherein the adjusting, based on the falling distance and the $j-1^{th}$ target region, the $j^{th}$ target region includes:
determining, based on the falling distance and the $j-1^{th}$ target region, an extension region corresponding to the $j^{th}$ target region; and
determining an adjusted $j^{th}$ target region based on the $j^{th}$ target region and the extension region corresponding to the $j^{th}$ target region.

17. A method for generating a treatment plan for irradiating, using a radiation system, a target region, implemented on a computing device having at least one processor and at least one storage device, the method comprising:
obtaining a target image of a subject, the subject including the target region;

determining, based on the target image, a plurality of sampling points in a vicinity of a boundary of the target region;

determining one or more dose control points by using at least one filter to filter the plurality of sampling points, each of the at least one filter including a first boundary and a second boundary, the first boundary being located inside the second boundary; and updating, based on the one or more dose control points, at least one parameter from the treatment plan, the at least one parameter relating to a dose region, wherein the dose region is enclosed by an isodose curve.

18. The method of claim 17, wherein the updating, based on the one or more dose control points, at least one parameter of the treatment plan includes:

obtaining an objective function corresponding to the target region, the objective function representing a conformity between the target region and the dose region; and updating the treatment plan by optimizing the at least one parameter such that the objective function satisfies an optimization condition.

19. A system for generating a treatment plan for irradiating, using a radiation system, a target region, comprising:

at least one storage device including a set of instructions; and at least one processor configured to communicate with the at least one storage device, wherein when executing the set of instructions, the at least one processor is configured to direct the system to perform operations including:

obtaining at least one parameter from the treatment plan, the least one parameter relating to a dose region, wherein the dose region is enclosed by an isodose curve;

obtaining an objective function corresponding to the target region, the objective function representing a conformity between the target region and the dose region, wherein the objective function includes at least one conformity parameter relating to a first volume of an intersection region between the target region and the dose region; and generating the treatment plan by optimizing the at least one parameter such that the objective function satisfies an optimization condition, wherein the first volume of the intersection region is determined by:

dividing the target region into a plurality of grid regions;

determining a dose of each of the plurality of grid regions of the target region;

identifying one or more grid regions from the plurality of grid regions of the target region, wherein for each of the one or more grid regions of the target region, a radiation dose of the grid region satisfies a first dose condition; and determining the first volume of the intersection region based on the one or more grid regions.

* * * * *